United States Patent [19]

Klotz

[11] 4,327,236
[45] Apr. 27, 1982

[54] HYDROCARBON-CONVERSION CATALYST AND ITS METHOD OF PREPARATION

[75] Inventor: Marvin R. Klotz, Batavia, Ill.

[73] Assignee: Standard Oil Company (Indiana), Chicago, Ill.

[21] Appl. No.: 182,796

[22] Filed: Aug. 29, 1980

Related U.S. Application Data

[60] Division of Ser. No. 54,958, Jul. 3, 1979, Pat. No. 4,268,420, which is a continuation-in-part of Ser. No. 897,360, Apr. 18, 1978, Pat. No. 4,269,813, which is a continuation-in-part of Ser. No. 733,267, Oct. 18, 1976, abandoned, and Ser. No. 819,974, Jul. 28, 1977, abandoned, and Ser. No. 836,403, Sep. 26, 1977, abandoned.

[51] Int. Cl.³ ...................... C10G 47/04; C10G 35/06
[52] U.S. Cl. .................................. 585/481; 585/475; 585/482; 208/110; 208/111; 208/136; 208/137
[58] Field of Search ...................... 585/481, 475, 482; 208/110, 111, 136, 137

[56] References Cited

U.S. PATENT DOCUMENTS

| | | | |
|---|---|---|---|
| 3,140,249 | 7/1964 | Plank et al. ........................... | 208/120 |
| 3,328,119 | 6/1967 | Robson ........................... | 585/481 X |
| 3,637,881 | 1/1972 | Williams et al. ...................... | 585/481 |
| 3,702,886 | 11/1972 | Arganer .............................. | 423/328 |
| 3,873,632 | 3/1975 | Pollitzer ............................ | 585/481 |
| 3,941,871 | 3/1976 | Dwyer et al. ........................ | 423/326 |
| 4,071,377 | 1/1978 | Schwuger et al. ..................... | 134/29 |

OTHER PUBLICATIONS

Proceedings of the Fifth Intl. Conf. on Zeolites, Naples, Italy, 2–6, Jun. 1960.

*Primary Examiner*—John F. Niebling
*Attorney, Agent, or Firm*—James L. Wilson; William T. McClain; William H. Magidson

[57] ABSTRACT

A new catalytic composition and its method of preparation are presented. The catalytic composition comprises a crystalline borosilicate and a porous refractory inorganic oxide, said borosilicate and said inorganic oxide having been intimately admixed with one another, said borosilicate comprising a molecular sieve material having the following composition in terms of mole ratios of oxides:

$$0.9 \pm 0.2\ M_{2/n}O{:}B_2O_3{:}YSiO_2{:}ZH_2O$$

wherein M is at least one cation having a valence of n, Y is between 4 and about 600, and Z is between 0 and about 160.

The catalytic composition can be used for the conversion of hydrocarbon streams, e.g., the isomerization of xylene feedstocks.

23 Claims, No Drawings

HYDROCARBON-CONVERSION CATALYST AND ITS METHOD OF PREPARATION

CROSS REFERENCE TO RELATED APPLICATIONS

This application is a division of application Ser. No. 59,958, filed July 3, 1979, now issued as U.S. Pat. No. 4,268,420 which is a continuation-in-part application of co-pending application U.S. Ser. No. 897,360, filed in the U.S. Patent and Trademark Office on Apr. 18, 1978, now issued as U.S. Pat. No. 4,269,813 said U.S. Ser. No. 897,360 being a continuation-in-part application of applications, U.S. Ser. No. 733,267, filed in the United States Patent and Trademark Office on Oct. 18, 1976, and now abandoned; U.S. Ser. No. 819,974, filed on July 28, 1977, and now abandoned; and U.S. Ser. No. 836,403, filed on Sept. 26, 1977, and now abandoned. Each of these applications is incorporated by reference herein and is made a part hereof, including but not limited to those portions of each which specifically appear hereinafter.

BACKGROUND OF THE INVENTION

1. Field of the Invention

This invention relates to novel crystalline borosilicates, catalysts containing such borosilicates, and a method for preparing such catalysts. More particularly, this invention relates to hydrocarbon-conversion catalysts that contain the crystalline borosilicates, a method for preparing such catalysts, and various hydrocarbon conversion processes using such crystalline borosilicates. Patent art that is relevant to such borosilicates can be found in U.S. Patent Classes 423-326, 252-458, and 260-668.

2. Description of the Prior Art

Zeolitic materials, both natural and synthetic, have been demonstrated in the past to have catalytic capabilities for many hydrocarbon processes. Zeolitic materials, often referred to as molecular sieves, are ordered porous crystalline aluminosilicates having a definite structure with large and small cavities interconnected by channels. The cavities and channels throughout the crystalline material are generally uniform in size allowing selective separation of hydrocarbons. Consequently, these materials in many instances have come to be classified in the art as molecular sieves and are utilized, in addition to the selective adsorptive processes, for certain catalytic properties. The catalytic properties of these materials are also affected, to some extent, by the size of the molecules which are allowed selectively to penetrate the crystal structure, presumably to be contacted with active catalytic sites within the ordered structure of these materials.

Generally, the term "molecular sieve" includes a wide variety of positive-ion-containing crystalline materials of both natural and synthetic varieties. They are generally characterized as crystalline aluminosilicates, although other crystalline materials are included in the broad definition. The crystalline aluminosilicates are made up of networks of tetrahedra of $SiO_4$ and $AlO_4$ moieties in which the silicon and aluminum atoms are cross-linked by the sharing of oxygen atoms. The electrovalence of the aluminum atom is balanced by the use of positive ions, for example, alkali-metal or alkaline-earth-metal cations.

Prior art developments have resulted in the formation of many synthetic crystalline materials. Crystalline aluminosilicates are the most prevalent and, as described in the patent literature and in the published journals, are designated by letters or other convenient symbols. Exemplary of these materials are Zeolite A (Milton, in U.S. Pat. No. 2,882,243), Zeolite X (Milton, in U.S. Pat. No. 2,882,244), Zeolite Y (Breck, in U.S. Pat. No. 3,130,007), Zeolite ZSM-5 (Argauer, et al., in U.S. Pat. No. 3,702,886), Zeolite ZSM-11 (Chu, in U.S. Pat. No. 3,709,979), Zeolite ZSM-12 (Rosinski, et al., in U.S. Pat. No. 3,832,449), and others.

Relevant art is the above U.S. Pat. No. 3,702,886, in which Argauer, et al., disclose the crystalline aluminosilicate Zeolite ZSM-5 and the method for making the same. This patent teaches the production of a zeolite wherein aluminum or gallium oxides are present in the crystalline structure, along with silicon or germanium oxides. A specific ratio of the latter to the former is reacted to produce a class of zeolites designated ZSM-5, which is limited to crystalline alumino- or gallo-silicates or germanates and which has a specified X-ray diffraction pattern. The above ZSM-11 and ZSM-12 patents are similarly limited to crystalline alumino- or gallo-silicates or germanates, also having specified X-ray diffraction patterns.

As shown by Haag, et al., in U.S. Pat. No. 3,856,871, by Morrison, in U.S. Pat. No. 3,856,872, by Burress, in U.S. Pat. No. 3,856,873, and by Hayward, in U.S. Pat. No. 3,856,874, such ZSM-type aluminosilicates are used suitably for the isomerization of xylenes.

Manufacture of the ZSM-type materials utilizes a mixed base system in which sodium aluminate and a silicon-containing material are mixed together with sodium hydroxide and an organic base, such as tetrapropylammonium hydroxide or tetrapropylammonium bromide, under specified reaction conditions, to form the desired crystalline aluminosilicate.

Dwyer, et al., in U.S. Pat. No. 3,941,871, claim and teach an organosilicate having very little aluminum in its crystalline structure and possessing an X-ray diffraction pattern similar to the ZSM-5 composition. This patent is considered relevant art.

Another relevant patent is U.S. Pat. No. 3,328,119, wherein Robson considers a synthetic crystalline aluminosilicate containing a minor amount of boria as an integral part of its crystal framework. This reference has been cited by the Examiner during the prosecution of the above-mentioned applications U.S. Ser. No. 819,974, now abandoned, and U.S. Ser. No. 836,403 now abandoned.

Additional relevant art comprises U.S. Pat. Nos. 3,329,480; 3,329,481; 4,029,716; and 4,078,009. Young, in U.S. Pat. Nos. 3,329,480 and 3,329,481, discloses "zircono-silicates" and "titano-silicates", respectively. Kaeding, in U.S. Pat. Nos. 4,029,716 and 4,078,009, discloses a crystalline aluminosilicate zeolite having a silica-to-alumina ratio of at least about 12 and a constraint index within the approximate range of 1 to 12, and having combined therewith boron in an amount of at least about 0.2 weight percent as a result of reaction of the zeolite with a boron-containing compound.

Unland, et al., in U.S. Pat. Nos. 4,115,424 and 4,140,726 disclose an improved alkylation catalyst that comprises a crystalline aluminosilicate exemplified by a type X- or Y-zeolite, which catalyst includes potassium, rubidium, and/or cesium cations and contains boron and/or phosphorus. The aluminosilicates are modified to have the potassium, rubidium, and/or cesium cations and the boron and/or phosphorus present. The boron or phosphorus components can be incorporated by inclusion in an ion exchange solution, or by subsequently utilizing a solution of such component as a slurrying medium for catalyst particles or as an impregnating medium to be absorbed in the catalyst.

Plank, et al., in U.S. Pat. Nos. 3,140,249; 3,140,251; and 3,140,253, disclose the suspension of a molecular sieve material in a matrix of a refractory inorganic oxide and its distribution throughout said matrix. The preparation and use of cation-exchanged molecular sieves are considered.

The present invention is directed to catalysts that comprise crystalline borosilicates and that can be used for the conversion of hydrocarbon streams, e.g., the isomerization of xylene feedstocks, and to the preparation of such catalysts.

SUMMARY OF THE INVENTION

According to the present invention, there are provided a catalytic composition that is suitable for the conversion of hydrocarbon streams, its method of preparation, and hydrocarbon conversion processes employing said catalytic composition. Broadly, the catalytic composition comprises a crystalline borosilicate and a porous refractory inorganic oxide, said borosilicate and said inorganic oxide having been intimately admixed with one another, said borosilicate comprising a molecular sieve material having the following composition in terms of mole ratios of oxides:

$$0.9 \pm 0.2 \ M_{2/n}O:B_2O_3:YSiO_2:ZH_2O$$

wherein M is at least one cation having a valence of n, Y is between 4 and about 600, and Z is between 0 and about 160. The catalytic composition can comprise a catalytic support comprising a crystalline borosilicate suspended in and distributed throughout a matrix of a refractory inorganic oxide, such as alumina, said support having been impregnated with at least one catalytically-active metal, and can be prepared by a specified method of preparation. Broadly, the method comprises: (1) admixing a crystalline borosilicate in a finely-divided state with a refractory inorganic oxide to form a catalytic support material, said catalytic support material having said borosilicate suspended in and distributed throughout a matrix of said inorganic oxide, said borosilicate comprising a molecular sieve material having the following composition in terms of mole ratios of oxides:

$$0.9 \pm 0.2 \ M_{2/n}O:B_2O_3:YSiO_2:ZH_2O$$

wherein M is at least one cation, n is the valence of the cation, Y is a value within the range of 4 to about 600, and Z is a value within the range of 0 to about 160; (2) impregnating said catalytic support material with a solution of a heat-decomposable compound of a catalytically-active metal to provide an impregnated material; (3) drying said impregnated material at a temperature of about 77° F. (25° C.) to about 392° F. (200° C.) for a period of about 10 minutes to about 100 hours in air to obtain a dried impregnated material; and (4) calcining said dried impregnated material at a temperature within the range of about 752° F. (400° C.) to about 1,112° F. (600° C.) for a period of about 10 minutes to about 20 hours to provide said catalytic composition.

The catalytic support material can be prepared by either of the following two techniques. It can be prepared, when the inorganic oxide is an alumina, by: (1) admixing said borosilicate in a finely-divided state with the alumina by mulling spray-dried alumina with 5 to 20 wt.% gamma-alumina hydrosol or beta-alumina trihydrate and with said borosilicate to form a mixture that is suitable for extruding; (2) adding water in an amount that will yield an extrudate having about 20 wt.% to about 50 wt.% water; (3) adding, if needed, an extrusion aid and a pore-diameter modifier; (4) extruding said resulting admixture to form an extruded admixture; (5) drying said extruded admixture in air at a temperature of about 77° F. (25° C.) to about 392° F. (200° C.) for a period of about 10 minutes to about 20 hours to obtain a dried extrudate; and (6) calcining said dried extrudate at a temperature within the range of about 752° F. (400° C.) to about 1,112° F. (600° C.) for a period of about 10 minutes to about 20 hours to provide a calcined catalytic support material.

Moreover, it can be prepared also by: (1) admixing said borosilicate in a finely-divided state with a hydrosol, sol, or hydrogel of said inorganic oxide in order to uniformly disperse said borosilicate in said hydrosol, sol, or hydrogel of said inorganic oxide to form an admixture; (2) while continually stirring the admixture, adding a gelling medium to promote gellation and to form a gel; (3) drying said gel at a temperature within the range of about 77° F. (25° C.) to about 392° F. (200° C.) for a period of about 10 minutes to about 100 hours in the presence of moving air to form a dried mixture; and (4) calcining said dried mixture at a temperature within the range of about 752° F. (400° C.) to about 1,112° F. (600° C.) for a period of about 20 minutes to about 20 hours to provide a calcined catalytic support material.

An alumina is a typical refractory inorganic oxide. Catalytically-active metals include, but are not limited to, metals of Group VIB of the Periodic Table of Elements, such as molybdenum, and metals of Group VIII of the Periodic Table of Elements, such as nickel. Such metals may be incorporated into the catalytic composition by impregnation and/or cation-exchange techniques.

There is also provided a process for the conversion of a hydrocarbon stream, which process comprises contacting said stream at conversion conditions with a catalytic composition of the present invention. In addition, there is provided a process for the catalytic isomerization of a xylene feed, which process comprises contacting said feed at isomerization conditions with a catalytic composition of the present invention.

DESCRIPTION AND PREFERRED EMBODIMENTS

The present invention relates to a catalytic composition employing a novel synthetic crystalline molecular sieve material, a crystalline borosilicate, a method for preparing said catalytic composition, and the use of said catalytic composition for the conversion of hydrocarbon streams.

The family of such crystalline borosilicate materials, which are identified as AMS-1B borosilicates, has a particular X-ray diffraction pattern as is shown in the various tables hereinafter. Such crystalline borosilicate can generally be characterized, in terms of the mole ratios of oxides, as follows in Equation I:

$$0.9 \pm 0.2 \, M_{2/n}O:B_2O_3:YSiO_2:ZH_2O \quad \text{(I)}$$

wherein M is at least one cation, n is the valence of the cation, Y is between 4 and about 600, and Z, representing the water present in such material, is between 0 and about 160, or more.

In another instance, the claimed crystalline borosilicate can be represented in terms of mole ratios of oxides for the crystalline material not yet activated or calcinated at high temperatures, as follows in Equation II:

$$0.9 \pm 0.2 \, [WR_2O + (1-W)M_{2/n}O]:B_2O_3:YSiO_2:ZH_2O \quad \text{(II)}$$

wherein R is an alkylammonium cation, M is at least one cation, n is the valence of the cation, Y is a value between 4 and 600, Z is a value between 0 and about 160, and W is a value greater than 0 and less than 1.

In Equation I, M can represent an alkali-metal cation, an alkaline-earth-metal cation, an ammonium cation, an alkylammonium cation, a hydrogen cation, a catalytically-active-metal cation, or mixtures thereof. In Equation II, M can represent an alkali-metal cation, an alkaline-earth-metal cation, an ammonium cation, a hydrogen cation, a catalytically-active-metal cation, or mixtures thereof.

Advantageously, the value for Y falls within the range of 4 to about 500. Suitably, Y is 4 to about 300; preferably, about 50 to about 160; and more preferably, about 80 to about 120.

Suitably, Z is within the range of 0 to about 40.

The original cation "M" in the above formulations can be replaced in accordance with techniques well known in the art, at least in part, by ion exchange with other cations. Preferred replacing cations include tetraalkylammonium cations, metal ions, ammonium ions, hydrogen ions, and mixtures of the above. Particularly preferred cations are those which render the AMS-1B crystalline borosilicate catalytically active especially for hydrocarbon conversion. These materials include hydrogen, rare earth metals, aluminum, metals of Groups IB, IIB and VIII of the Periodic Table, noble metals, manganese, etc., and other catalytically active materials and metals known to the art. The catalytically active components can be present anywhere from about 0.05 to about 25 weight percent of the AMS-1B crystalline borosilicate.

Members of the family of AMS-1B crystalline borosilicates possess a specified and distinguishing crystalline structure. Two methods were employed to obtain X-ray diffraction patterns of various samples of AMS-1B crystalline borosilicates.

In the first method, identified hereinafter as Method No. 1, a Phillips instrument which utilized copper K alpha radiation was employed. The X-ray diffraction intensities versus two-theta were recorded on a strip chart using a proportional counter. The theta values recorded were converted to interplanar spacing values in Angstroms (Å) using the Bragg equation. The relative intensities (relative peak heights) were calculated as (100 $I/I_o$), where $I_o$ is the intensity of the strongest recorded peak and I is the value actually read for the particular interplanar spacing.

In the second method, identified hereinafter as Method No. 2, the X-ray diffractometer was a Phillips instrument which utilized copper K alpha radiation in conjunction with an AMR focusing monochromometer and a theta compensating slit, in which its aperture varies with the theta angle. The output from the diffractometer was processed through a Canberra hardware/software package and reported by way of a strip chart and tabular printout. The compensating slit and the Canberra package tend to increase the peak/background ratios while reducing the peak intensities at low theta angles [large interplanar spacings] and increasing the peak intensities at high theta angles [small interplanar spacings].

For ease of reporting the results obtained by either method, the relative intensities (relative peak heights) were arbitrarily assigned the following values:

| Relative Peak Height | Assigned Strength |
|---|---|
| less than 10 | VW (very weak) |
| 10–19 | W (weak) |
| 20–39 | M (Medium) |
| 40–70 | MS (medium strong) |
| greater than 70 | VS (very strong) |

These assigned strengths are used throughout this application.

An X-ray diffraction pattern obtained by means of Method No. 1 and displaying the significant lines in the indicated relative intensities (relative peak heights) and assigned strength for the AMS-1B crystalline borosilicates is presented in Table I hereinbelow:

TABLE I

| Interplanar Spacings, d(Å) | Relative Intensity ($I/I_o$) | Assigned Strength |
|---|---|---|
| 11.04 ± 0.2 | 100 | VS |
| 10.04 ± 0.2 | 68 | MS |
| 7.37 ± 0.15 | 2 | VW |
| 6.70 ± 0.1 | 7 | VW |
| 6.32 ± 0.1 | 10 | W |
| 5.98 ± 0.07 | 20 | M |
| 5.68 ± 0.07 | 10 | W |
| 5.53 ± 0.05 | 13 | W |
| 5.30 ± 0.05 | 3 | VW |
| 5.21 ± 0.05 | 3 | VW |
| 4.98 ± 0.05 | 9 | VW |
| 4.62 ± 0.05 | 3 | VW |
| 4.37 ± 0.05 | 5 | VW |
| 4.27 ± 0.05 | 10 | W |
| 4.07 ± 0.05 | 2 | VW |
| 4.00 ± 0.05 | 6 | VW |
| 3.83 ± 0.05 | 84 | VS |
| 3.72 ± 0.05 | 48 | MS |
| 3.64 ± 0.05 | 23 | M |
| 3.42 ± 0.05 | 9 | VW |
| 3.30 ± 0.05 | 11 | W |
| 3.23 ± 0.05 | 3 | VW |
| 3.16 ± 0.05 | 2 | VW |
| 3.12 ± 0.05 | 2 | VW |
| 3.04 ± 0.05 | 9 | VW |
| 2.98 ± 0.02 | 16 | W |
| 2.94 ± 0.02 | 10 | W |
| 2.86 ± 0.02 | 2 | VW |
| 2.83 ± 0.02 | 1 | VW |
| 2.73 ± 0.02 | 3 | VW |
| 2.59 ± 0.02 | 3 | VW |
| 2.55 ± 0.02 | 3 | VW |
| 2.51 ± 0.02 | 3 | VW |
| 2.48 ± 0.02 | 5 | VW |
| 2.45 ± 0.02 | 3 | VW |
| 2.39 ± 0.02 | 5 | VW |
| 2.00 ± 0.02 | 13 | W |
| 1.99 ± 0.02 | 14 | W |
| 1.94 ± 0.02 | 6 | VW |
| 1.91 ± 0.02 | 4 | VW |
| 1.86 ± 0.02 | 2 | VW |
| 1.81 ± 0.02 | 1 | VW |
| 1.75 ± 0.02 | 2 | VW |
| 1.66 ± 0.02 | 4 | VW |
| 1.56 ± 0.02 | 2 | VW |

When Method No. 1 is employed, the above X-ray pattern is characteristic of the AMS-1B crystalline borosilicate having the oxide mole formula described in Equation I, which borosilicate has been calcined at 1,100° F. (593° C.) and wherein the tetraalkylammonium ion has been removed from the system by the calcination procedure.

In the following Table, the more significant interplanar spacings and their assigned strengths are summarized from Table I.

TABLE II

| Interplanar Spacings, d(Å) | Assigned Strength |
|---|---|
| 11.04 ± 0.2 | VS |
| 10.04 ± 0.2 | MS |
| 5.98 ± 0.07 | M |
| 3.83 ± 0.05 | VS |
| 3.72 ± 0.05 | MS |
| 3.64 ± 0.05 | M |

In instances in which the AMS-1B crystalline borosilicate in an as-produced state (prior to high temperature calcination, but after some reasonable amount of drying has taken place), is analyzed by X-ray diffraction analysis by Method No. 1, the crystalline borosilicate generally is characterized by Equation II above and has an X-ray diffraction pattern showing the following significant lines:

TABLE III

| Interplanar Spacing, d(Å) | Assigned Strength |
|---|---|
| 11.04 ± 0.2 | MS |
| 9.82 ± 0.2 | MS |
| 9.60 ± 0.2 | MW |
| 8.84 ± 0.2 | VW |
| 7.37 ± 0.2 | W |
| 7.02 ± 0.15 | VW |
| 6.60 ± 0.1 | VW |
| 6.32 ± 0.1 | W |
| 5.90 ± 0.07 | W |
| 5.68 ± 0.07 | W |
| 5.53 ± 0.05 | W |
| 5.27 ± 0.05 | VW |
| 5.09 ± 0.05 | VW |
| 4.95 ± 0.05 | W |
| 4.57 ± 0.05 | W |
| 4.44 ± 0.05 | VW |
| 4.35 ± 0.05 | W |
| 4.23 ± 0.05 | W |
| 4.04 ± 0.05 | VW |
| 3.97 ± 0.05 | W |
| 3.80 ± 0.05 | VS |
| 3.72 ± 0.05 | M |
| 3.67 ± 0.05 | MS |
| 3.60 ± 0.05 | MS |
| 3.45 ± 0.05 | VW |
| 3.41 ± 0.05 | W |
| 3.30 ± 0.05 | W |
| 3.28 ± 0.05 | W |
| 3.23 ± 0.05 | VW |
| 3.16 ± 0.05 | VW |
| 3.12 ± 0.05 | VW |
| 3.06 ± 0.05 | W |
| 2.96 ± 0.02 | W |
| 2.94 ± 0.02 | W |
| 2.85 ± 0.02 | VW |
| 2.76 ± 0.02 | VW |
| 2.71 ± 0.02 | W |
| 2.59 ± 0.02 | W |
| 2.56 ± 0.02 | VW |
| 2.49 ± 0.02 | VW |
| 2.47 ± 0.02 | W |
| 2.40 ± 0.02 | VW |
| 2.38 ± 0.02 | W |
| 2.33 ± 0.02 | VW |
| 2.31 ± 0.02 | VW |
| 2.28 ± 0.02 | VW |
| 2.21 ± 0.02 | VW |

TABLE III-continued

| Interplanar Spacing, d(Å) | Assigned Strength |
|---|---|
| 2.19 ± 0.02 | VW |
| 2.16 ± 0.02 | VW |
| 2.10 ± 0.02 | VW |
| 2.06 ± 0.02 | VW |
| 2.00 ± 0.02 | W |
| 1.99 ± 0.02 | W |
| 1.94 ± 0.02 | W |
| 1.90 ± 0.02 | W |
| 1.86 ± 0.02 | W |
| 1.82 ± 0.02 | VW |
| 1.75 ± 0.02 | W |
| 1.71 ± 0.02 | VW |
| 1.66 ± 0.02 | W |

In the following Table, the more significant interplanar spacings and their assigned strengths are summarized from Table III.

TABLE IV

| Interplanar Spacing, d(Å) | Assigned Strength |
|---|---|
| 11.04 ± 0.2 | MS |
| 9.82 ± 0.2 | MS |
| 3.80 ± 0.05 | VS |
| 3.72 ± 0.05 | M |
| 3.67 ± 0.05 | MS |
| 3.60 ± 0.05 | MS |

A typical X-ray diffraction pattern obtained by means of Method No. 2 and displaying the significant lines which have relative intensities (relative peak heights) of 11 or higher for an AMS-1B crystalline borosilicate after calcination at 1,000° F. (538° C.) is shown in Table V hereinbelow.

TABLE V

| Interplanar Spacing, d(Å) | Relative Intensity | Assigned Strength |
|---|---|---|
| 11.3 ± 0.2 | 38 | M |
| 10.1 ± 0.2 | 30 | M |
| 6.01 ± 0.07 | 14 | W |
| 4.35 ± 0.05 | 11 | W |
| 4.26 ± 0.05 | 14 | W |
| 3.84 ± 0.05 | 100 | VS |
| 3.72 ± 0.05 | 52 | MS |
| 3.65 ± 0.05 | 31 | M |
| 3.44 ± 0.05 | 14 | W |
| 3.33 ± 0.05 | 16 | W |
| 3.04 ± 0.05 | 16 | W |
| 2.97 ± 0.02 | 22 | M |
| 2.48 ± 0.02 | 11 | W |
| 1.99 ± 0.02 | 20 | M |
| 1.66 ± 0.02 | 12 | W |

An AMS-1B borosilicate which has been only subjected to mild drying at 165° C. (as produced material) possesses an X-ray diffraction pattern obtained by Method No. 2, which pattern has the following significant lines:

TABLE VI

| Interplanar Spacing, d(Å) | Relative Intensity | Assigned Strength |
|---|---|---|
| 11.4 ± 0.2 | 19 | W |
| 10.1 ± 0.2 | 17 | W |
| 3.84 ± 0.05 | 100 | VS |
| 3.73 ± 0.05 | 43 | MS |
| 3.66 ± 0.05 | 26 | M |
| 3.45 ± 0.05 | 11 | W |
| 3.32 ± 0.05 | 13 | W |
| 3.05 ± 0.05 | 12 | W |
| 2.98 ± 0.02 | 16 | W |
| 1.99 ± 0.02 | 10 | W |

TABLE VI-continued

| Interplanar Spacing, d(Å) | Relative Intensity | Assigned Strength |
|---|---|---|
| 1.66 ± 0.02 | 20 | M |

As discussed in Example XII of the parent application, U.S. Pat. No. 4,269,813, the X-ray diffraction patterns of crystalline AMS-1B borosilicates can be represented by general terms by the information shown in the following Table VII:

TABLE VII

X-ray Diffraction Pattern of AMS-1B Borosilicates

| Interplanar Spacings | Assigned Strengths For | |
|---|---|---|
| | All | Calcined at 1,000° F.–1,100° F. |
| 11.2 ± 0.2 | W-VS | M-VS |
| 10.0 ± 0.2 | W-MS | M-MS |
| 5.97 ± 0.07 | W-M | W-M |
| 3.82 ± 0.05 | VS | VS |
| 3.70 ± 0.05 | MS | MS |
| 3.62 ± 0.05 | M-MS | MS |
| 2.97 ± 0.02 | W-M | W-M |
| 1.99 ± 0.02 | VW-M | VW-M |

Therefore, in broad terms, the X-ray diffraction patterns of crystalline AMS-1B borosilicates comprise the interplanar spacings shown in Table VII and the assigned strengths shown therein depending upon the presence or absence of calcination of the material prior to X-ray diffraction analysis.

The AMS-1B crystalline borosilicates of the present invention are useful as catalysts for various hydrocarbon conversion processes and they are suitable for chemical adsorption. Some of the hydrocarbon conversion processes for which the borosilicates appear to have relatively useful catalytic properties are fluidized catalytic cracking; hydrocracking; the isomerization of normal paraffins and naphthenes; the reforming of naphthas and gasoline-boiling-range feedstocks; the isomerization of aromatics, especially the isomerization of alkylaromatics, such as xylenes; the disproportionation of aromatics, such as toluene, to form mixtures of other more valuable products including benzene, xylene, and other higher methyl substituted benzenes; hydrotreating; alkylation; hydrodealkylation; hydrodesulfurization; and hydrodenitrogenation. They are particularly suitable for the isomerization of alkylaromatics, such as xylenes, and for the conversion of ethylbenzene. The AMS-1B borosilicates, in certain ion-exchanged forms, can be used to convert alcohols, such as methanol, to useful products, such as aromatics or olefins.

When the AMS-1B crystalline borosilicate is used as a hydrocracking catalyst, hydrocracking charge stocks can pass over the catalyst at temperatures anywhere from about 500° F. (260° C.) to about 850° F. (454° C.) or higher using known molar ratios of hydrocarbon to hydrogen and varying pressures anywhere from a few up to many thousands of pounds per square inch, or higher. The weight hourly space velocity and other process parameters can be varied consistent with the well-known teachings of the art.

The specified AMS-1B crystalline borosilicate is also suitable as a reforming catalyst to be used with the appropriate hydrogenation components at well-known reforming conditions including temperatures of anywhere from about 500° F. (260° C.) to about 1,050° F. (566° C.), or more, pressures anywhere from a few up to 300 psig (2,172 KPa) to 1,000 psig (6,998 KPa), and weight hourly space velocities and hydrogen-to-hydrocarbon mole ratios consistent with those well known in the reforming art.

The present crystalline borosilicate is also suitable for hydrocarbon isomerization and disproportionation. It is especially useful for liquid or vapor phase isomerization of xylenes and especially the isomerization of mixed xylenes to predominantly paraxylene products. Operating conditions for the isomerization of a xylene feed broadly comprise a temperature of about 200° F. (93° C.) to about 1,000° F. (538° C.), a hydrogen-to-hydrocarbon mole ratio of about 0 to about 20, a weight hourly space velocity (WHSV) of about 0.01 weight unit of feed per hour per weight unit of catalyst ($hr^{-1}$) to about 90 $hr^{-1}$, and a pressure of about 0 psig (101 KPa) to about 1,000 psig (6,998 KPa). Advantageously, the conditions comprise a temperature of about 400° F. (204° C.) to about 900° F. (482° C.), a hydrogen-to-hydrocarbon mole ratio of about 1 to about 12, a WHSV of about 1 $hr^{-1}$ to about 20 $hr^{-1}$, and a pressure of about 10 psig (170 KPa) to about 500 psig (3,551 KPa). The preferred conditions for the isomerization of xylenes comprise a temperature of about 600° F. (316° C.) to about 850° F. (454° C.), a hydrogen-to-hydrocarbon mole ratio of about 2 to about 8, a WHSV of about 1 $hr^{-1}$ to about 10 $hr^{-1}$, and a pressure of about 100 psig (793 KPa) to about 300 psig (2,172 KPa).

The choice of catalytically active metals to be placed on the AMS-1B crystalline borosilicate can be selected from any of those well known in the art. Nickel seems to be especially appropriate for isomerization of aromatics. When used as a catalyst in isomerization processes with suitable cations placed on the ion-exchangeable sites within the AMS-1B crystalline borosilicate, reasonably high selectivities for production of desired isomers are obtained.

The claimed AMS-1B crystalline borosilicates can also be used as adsorbents to selectively adsorb specific isomers or hydrocarbons in general from a liquid or vapor stream, such as alcohols from water.

The ability for these materials to be stable under high temperatures or in the presence of other normal deactivating agents appears to make this class of crystalline materials relatively valuable for high-temperature operations including the cyclical types of fluidized catalytic cracking or other processing.

The AMS-1B crystalline borosilicates can be used as catalysts or as adsorbents whether in the alkali-metal or alkaline-earth-metal forms, the ammonium form, the hydrogen form, or any other univalent or multivalent cationic form. Mixtures of cations may be employed. The AMS-1B crystalline borosilicates can also be used in intimate combination with a hydrogenating component, such as tungsten, vanadium, molybdenum, rhenium, nickel, cobalt, chromium, manganese, or a noble metal, such as platinum or palladium, or rare earth metals, where a hydrogenation-dehydrogenation function is to be performed. Such components can be exchanged into the composition at the cationic sites, represented by the term "M" in the above formulae, impregnated therein, or physically intimately admixed therewith. In one example, platinum can be placed on the borosilicate with a platinum-metal-containing ion.

The impregnation of a hydrogenation metal on the borosilicate or on a support comprising the crystalline borosilicate suspended in and distributed throughout a matrix of a porous refractory inorganic oxide, such as an alumina, often results in a suitable catalytic composition. For example, a catalyst comprising molybdenum impregnated on a composition of AMS-1B crystalline borosilicate suspended in an alumina matrix, when used to isomerize a feed of mixed xylenes, furnishes better selectivity and higher by-product values.

The original cation associated with the AMS-1B crystalline borosilicate can be replaced, as mentioned above, by a wide variety of other cations according to techniques which are known in the art. Ion exchange techniques known in the art are disclosed in many patents, including U.S. Pat. No. 3,140,249, U.S. Pat. No. 3,140,251, and U.S. Pat. No. 3,140,253, the teachings of which are incorporated by reference into this specification.

A catalytically active material can be placed onto the borosilicate structure by ion exchange, impregnation, or other suitable contact means, followed by washing, drying at about 150° F. (66° C.) to about 600° F. (316° C.), and then calcining in a suitable atmosphere, such as air, nitrogen, other gases, or combinations thereof, at about 500° F. (260° C.) to about 1,500° F. (816° C.), typically about 1,000° F. (538° C.), usually for about 0.5 hour to about 20 hours. This procedure can be repeated one or more times. Advantageously, before placing a catalytically active metal ion on the borosilicate structure, the borosilicate is in the hydrogen form which, typically, is produced by exchange with ammonium ion followed by calcination.

Ion-exchange within the cationic site within the crystalline material will generally have a relatively insignificant effect on the overall X-ray diffraction pattern that the crystalline borosilicate material generates. Small variations may occur at various spacings on the X-ray pattern, but the overall pattern remains essentially the same. Small changes in the X-ray diffraction patterns can also be the result of processing differences during manufacture of the borosilicate; however, the material will still fall within the generic class of AMS-1B crystalline borosilicates defined in terms of their X-ray diffraction patterns as shown in the tables found herein, or in the examples that follow.

The crystalline borosilicate of the present invention can be incorporated as a pure borosilicate in a catalyst or adsorbent or can be admixed with various binders or bases depending upon the intended process use. In many instances, the crystalline borosilicate can be pelletized or extruded. The crystalline borosilicate can be combined with active or inactive materials, synthetic or naturally-occurring zeolites, as well as inorganic or organic materials which would be useful for binding the borosilicate. Other well-known materials include mixtures of silica, silica-alumina, alumina sols, clays, such as bentonite or kaolin, or other binders well known in the art. The crystalline borosilicate can also be mixed intimately with porous matrix materials, such as silica-zirconia, silica-magnesia, silica-alumina, silica-thoria, silica-beryllia, silica-titania, as well as three component compositions including, but not limited to, silica-alumina-thoria and many other materials well known in the art. The crystalline borosilicate content can vary anywhere from a few up to 100 wt.% of the total finished product. Typical catalytic compositions contain about 5 wt.% to about 80 wt.% borosilicate material.

The AMS-1B crystalline borosilicate generally can be prepared by mixing an aqueous medium of oxides of boron, an alkali metal or an alkaline earth metal, such as sodium, and silicon, together with alkylammonium cations or a precursor of alkylammonium cations, such as an alkylamine, an alkylamine plus an alkyl hydroxide, an alkylamine plus an alkyl halide, or an alkylamine plus an alkyl acetate. The alkyl groups in the alkylammonium cations may be the same, or mixed, such as tetraethyl-, or diethyl-dipropyl-ammonium cations. The mole ratios of the various reactants can be varied considerably to produce the AMS-1B crystalline borosilicates. In particular, the mole ratios of the initial reactant concentrations for producing the borosilicate can vary as is indicated in Table VIII below.

Examples of oxides of boron are $H_3BO_3$, $B_2O_3$, and $B_4O_7$. Examples of oxides of silicon are silicic acid, sodium silicate, tetraalkyl silicates, and Ludox, which is a stabilized polymer of silicic acid manufactured by E. I. duPont de Nemours & Co. Suitable compounds of the alkali metals or alkaline earth metals are their hydroxides.

TABLE VIII

| | Broad | Preferred | Most Preferred |
|---|---|---|---|
| $SiO_2/B_2O_3$ | 5–400 | 10–150 | 10–80 |
| $R_2O+/(R_2O+ + M_{2/n}O)$ | 0.1–1 | 0.2–0.97 | 0.3–0.97 |
| $OH^-/SiO_2$ | 0.01–11 | 0.1–2 | 0.1–1 |
| $H_2O/OH^-$ | 10–4,000 | 10–500 | 10–500 | where R is an alkylamine or alkylammonium cation, preferably tetra-n-propyl ammonium cation or tetraethyl ammonium cation, and M is at least one cation having the valence of n, such as an alkali-metal or an alkaline-earth-metal cation. The above quantities can be varied in concentration in the aqueous medium.

During preparation, acidic conditions generally should be avoided. When ammonium hydroxide is used as a base, borosilicates can be produced with initial pH's of 5.8, or lower. When alkali metal hydroxides are used, the values of the ratio of $OH^-/SiO_2$ in Table VIII should furnish a pH of the system that broadly falls within the range of about 9 to about 13.5. Advantageously, the pH of the reaction system falls within the range of about 10.5 to about 11.5. Preferably, the pH of the system is about 10.8 to about 11.2. A proper pH is conducive to the incorporation of boron into the molecular sieve structure.

By simple regulation of the quantity of boron (represented as $B_2O_3$) in the reaction mixture, it is possible to vary the $SiO_2/B_2O_3$ molar ratio in the final product in a range of from about 40 to about 600, or more. In instances where an effort is made to minimize aluminum in the borosilicate crystal structure, the molar ratios of $SiO_2/Al_2O_3$ can easily exceed a ratio of 2,000:1 to 3,000:1 or more. This ratio is generally only limited by the availability of aluminum-free raw materials.

Molar ratios of $SiO_2/B_2O_3$ in the final crystalline product can vary from 4 to about 600, or more. Actual laboratory preparations under the general conditions described herein produce $SiO_2/B_2O_3$ molar ratios starting around 60 or lower. Lower ratios might be produced using production methods which still are in the scope of the teachings of this specification.

Unit cell measurements of the AMS-1B crystalline borosilicates showed a linear decrease of the unit cell size with respect to an increasing boron concentration in the molecular sieve over a $SiO_2/B_2O_3$ range of about 80 to about 600. Ion-exchange in the AMS-1B borosilicate has shown also that there is one equivalent of alkali metal or alkaline earth metal per mole of boron, as required for electrovalent neutrality.

Under reasonably controlled conditions using the above information the claimed AMS-1B crystalline borosilicate will be produced. Typical reaction conditions include heating the reactants to a temperature of anywhere from about 77° F. (25° C.) to about 572° F. (300° C.), or higher, for a period of time of anywhere from about one hour to four weeks, or more. Preferred temperature ranges are anywhere from about 194° F. (90° C.) to about 482° F. (250° C.) with an amount of time necessary for the precipitation of the AMS-1B crystalline borosilicate. A preferred reaction time varies from about 4 hours to about 2 weeks. A more preferred temperature varies from about 212° F. (100° C.) to about 482° F. (250° C.) and more preferred reaction time varies from about 6 hours to about 1 week. Especially preferred conditions include a temperature around 329° F. (165° C.) for a period of about 5 days.

The material thus formed can be separated and recovered by well-known means, such as filtration. This material can be mildly dried for anywhere from a few hours to a few days at varying temperatures to form a dry cake which itself can then be crushed to a powder or to small particles and extruded, pelletized, or made into forms suitable for its intended use. Typically, the material prepared after the mild drying conditions will contain the alkylammonium ion within the solid mass and a subsequent activation or calcination procedure is necessary, if it is desired to remove this material from the formed product.

Typically, the high temperature calcination conditions will take place at temperatures anywhere from about 500° F. (260° C.) to about 1,600° F. (871° C.), or higher. Extreme calcination temperatures may prove detrimental to the crystal structure or may totally destroy it. There is generally no need for going beyond about 1,100° F. (593° C.) in order to remove the alkylammonium cation from the original crystalline material formed.

In a typical preparation of an AMS-1B crystalline borosilicate, a compound of an alkali metal or an alkaline earth metal, such as sodium hydroxide, and a compound of boron, such as boric acid, are dissolved in water (preferably, distilled or deionized water). A tetraalkylammonium compound, such as tetra-n-propylammonium bromide, is added to the above solution and the pH of the resulting solution is adjusted to a value of about 11.0±0.2 by the addition of base or acid. A compound of silicon, such as silica sol, is added rapidly to the solution, while the solution is being agitated vigorously. Vigorous agitation is continued for about 15 minutes. After the pH of the resulting solution is adjusted to about 11.0±0.2, it is placed in an autoclave that is maintained at a temperature of about 329° F. (165° C.). Preferably, a stirred autoclave is used. The solution is kept in the autoclave for about 5 days for crystallization. It is preferred that the crystallization temperature be maintained below the decomposition temperature of the tetraalkylammonium compound. At the completion of the crystallization, the crystalline molecular sieve is removed from the autoclave, filtered, and washed with water. The molecular sieve material is dried in a forced draft oven at 230° F. (110° C.) for about 16 hours and is then heated in air in a manner such that the temperature rise does not exceed 200° F. (111° C.) per hour until a temperature of about 1,000° F. (538° C.) is reached. Calcination at this temperature is then continued for about 4 hours.

Typically, the surface area of the resulting molecular sieve, as determined by BET surface area analysis, is about 350 m²/gm to about 390 m²/gm and the sieve particles have a maximum diameter, as determined by a scanning electron microscope, of about 2 microns.

Typically, an active hydrocarbon conversion catalyst is prepared by ion-exchanging a borosilicate, as prepared above, one or more times with an aqueous solution of ammonium acetate at a temperature of about 185° F. (85° C.) to about 212° F. (100° C.) and drying, as described above, the ion-exchanged molecular sieve. The borosilicate is converted to the hydrogen form by calcination. Then, if desired, the metallic cations, for example, nickel ions, are introduced onto the borosilicate, typically, by exchanging the sieve one or more times with an aqueous solution of a compound of the metal, for example, nickelous nitrate or the ammonia complex of nickel, at a temperature of about 185° F. (85° C.) to about 212° F. (100° C.). Subsequently, the catalyst composition is formed by dispersing the finely-divided metal-exchanged borosilicate in a sol or gel of a high-grade-purity gamma-alumina and adding, while stirring, a solution of ammonium hydroxide to promote gellation. The resulting mixture is dried and calcined, as described above, pulverized to a convenient particle size, and formed into pellets or extrudate.

Alternatively, the original finely-divided unexchanged crystalline borosilicate can be dispersed in the sol or gel of the refractory inorganic oxide, such as alumina, the mixture gelled, dried, and calcined, and the cation-exchanging performed prior to or after the drying and/or calcination.

In an alternate method, the catalyst composition can be formed by mulling spray-dried alumina with 5 to 20 wt.% gamma-alumina hydrosol or beta-alumina trihydrate and with the finely-divided borosilicate to form a mixture that is suitable for extruding, adding water to the mixture, if needed, to provide an extrudate having about 20 wt.% to about 50 wt.% water, extruding, drying, and calcining.

Of course, a desired hydrogenation metal can be impregnated onto any of the above three compositions.

A broad embodiment of the crystalline borosilicate that is employed in the catalytic composition of the present invention is a crystalline borosilicate which comprises a molecular sieve material having the following composition in terms of mole ratios of oxides:

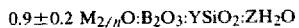
$$0.9\pm0.2\ M_{2/n}O:B_2O_3:YSiO_2:ZH_2O$$

wherein M is at least one cation having a valence of n, Y is between 4 and about 600, and Z is between 0 and about 160.

In another embodiment, the borosilicate is a crystalline borosilicate which comprises a molecular sieve material having the following composition in terms of mole ratios of oxides:

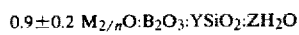
$$0.9\pm0.2\ M_{2/n}O:B_2O_3:YSiO_2:ZH_2O$$

wherein M is at least one cation having a valence of n, Y is between 4 and 600, and Z is between 0 and about 160, and providing an X-ray diffraction pattern comprising the following X-ray diffraction lines and assigned strengths:

| d(Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

Broadly, according to the present invention, there is provided a catalytic composition which comprises a cyrstalline borosilicate and a porous refractory inorganic oxide, said borosilicate and said inorganic oxide having been intimately admixed with one another, said borosilicate comprising a molecular sieve material having the following composition in terms of mole ratios of oxides:

$$0.9 \pm 0.2 \text{ M}_{2/n}\text{O}:\text{B}_2\text{O}_3:\text{YSiO}_2:\text{ZH}_2\text{O}$$

wherein M is at least one cation having a valence of n, Y is between 4 and about 600, and Z is between 0 and about 160.

In one embodiment of the catalytic composition of the present invention, there is provided a catalytic composition which comprises a crystalline borosilicate and a porous refractory inorganic oxide, said borosilicate and said inorganic oxide having been intimately admixed with one another, said borosilicate comprising a molecular sieve material having the following composition in terms of mole ratios of oxides:

$$0.9 \pm 0.2 \text{ M}_{2/n}\text{O}:\text{B}_2\text{O}_3:\text{YSiO}_2:\text{ZH}_2\text{O}$$

wherein M is at least one cation having a valence of n, Y is between 4 and about 600, and Z is between 0 and about 160, and said borosilicate providing an X-ray diffraction pattern comprising the following X-ray diffraction lines and assigned strengths:

| d(Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

In another embodiment, there is provided a catalytic composition which comprises a crystalline borosilicate and a porous refractory inorganic oxide, said borosilicate and said inorganic oxide having been intimately admixed with one another after said borosilicate has been calcined, and said borosilicate comprising a molecular sieve material providing an X-ray diffraction pattern comprising the following X-ray diffraction lines and assigned strengths:

| d(Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

$$0.9 \pm 0.2 \text{ M}_{2/n}\text{O}:\text{B}_2\text{O}_3:\text{YSiO}_2:\text{ZH}_2\text{O}$$

wherein M is at least one cation having a valence of n, Y is between 4 and about 600, and Z is between 0 and about 160.

In still another embodiment of the catalytic composition of the present invention, there is provided a catalytic composition which comprises at least one catalytically-active metal and a catalytic support comprising a crystalline borosilicate suspended in and distributed throughout a matrix of a refractory inorganic oxide, which composition has been prepared by the method which comprises: (1) admixing said borosilicate in a finely-divided state with a hydrosol, sol, or hydrogel of said inorganic oxide in order to uniformly disperse said borosilicate in said hydrosol, sol, or hydrogel of said inorganic oxide to form an admixture, said borosilicate comprising a molecular sieve material having the following composition in terms of mole ratios of oxides:

$$0.9 \pm 0.2 \text{ M}_{2/n}\text{O}:\text{B}_2\text{O}_3:\text{YSiO}_2:\text{ZH}_2\text{O},$$

wherein M is at least one cation, n is the valence of the cation, Y is a value within the range of 4 to about 600, and Z is a value within the range of 0 to about 160; (2) while continually stirring the admixture, adding a gelling medium to promote gellation and to form a gel; (3) drying said gel at a temperature of about 77° F. (25° C.) to about 392° F. (200° C.) for a period of about 10 minutes to about 100 hours in the presence of air to form a dried mixture; (4) calcining said dried mixture by heating said dried mixture in air at a maximum rate of about 200° F. per hour (111° C. per hour) to a calcination temperature within the range of about 752° F. (400° C.) to about 1,112° F. (600° C.) and maintaining said dried material at said calcination temperature for a period of about 30 minutes to about 20 hours to provide a calcined catalytic support material; (5) impregnating said calcined catalytic support material with an aqueous solution of a heat-decomposable compound of said catalytically-active metal to provide an impregnated material; (6) drying said impregnated material at a temperature of about 77° F. (25° C.) to about 392° F. (200° C.) for a period of about 10 minutes to about 100 hours in air to obtain a dried impregnated material; and (7) calcining said dried impregnated material by heating said dried impregnated material in air at a maximum rate of about 200° F. per hour (111° C. per hour) to a calcination temperature within the range of about 752° F. (400° C.) to about 1,112° F. (600° C.) and maintaining said dried impregnated material at said calcination temperature for a period of about 30 minutes to about 20 hours to provide said catalytic composition.

Moreover, according to the present invention, there is provided a method for the preparation of a catalytic composition that is suitable for the conversion of hydrocarbon streams, which method comprises: (1) admixing a crystalline borosilicate in a finely-divided state with a refractory inorganic oxide to form a catalytic support material, said catalytic support material having said borosilicate suspended in and distributed throughout a matrix of said inorganic oxide, said borosilicate comprising a molecular sieve material having the following composition in terms of mole ratios of oxides:

$$0.9 \pm 0.2 M_{2/n}O:B_2O_3:YSiO_2:ZH_2O$$

wherein M is at least on cation, n is the valence of the cation, Y is a value within the range of 4 to about 600, and Z is a value within the range of 0 to about 160; (2) impregnating said catalytic support material with a solution of a heat-decomposable compound of a catalytically-active metal to provide an impregnated material; (3) drying said impregnated material at a temperature of about 77° F. (25° C.) to about 392° F. (200° C.) for a period of about 10 minutes to about 100 hours in moving air to obtain a dried impregnated material; and (4) calcining said dried impregnated material at a temperature within the range of about 752° F. (400° C.) to about 1,112° F. (600° C.) for a period of about 30 minutes to about 20 hours to provide said catalytic composition.

The catalytic support material can be prepared by either of two methods. In one, wherein the inorganic oxide is an alumina, the catalytic support material is prepared by: (1) admixing said borosilicate in a finely-divided state with said alumina by mulling spray-dried alumina with 5 to 20 wt.% gamma-alumina hydrosol or beta-alumina trihydrate and with said borosilicate to form a mixture that is suitable for extruding; (2) adding water in an amount that will yield an extrudate having about 20 wt.% to about 50 wt.% water; (3) adding, if needed, an extrusion aid and a pore-diameter modifier; (4) extruding said resulting admixture to form an extruded admixture; (5) drying said extruded admixture in air at a temperature of about 77° F. (25° C.) to about 392° F. (200° C.) for a period of about 10 minutes to about 20 hours to obtain a dried extrudate; and (6) calcining said dried extrudate at a temperature within the range of about 752° F. (400° C.) to about 1,112° F. (600° C.) for a period of about 30 minutes to about 20 hours to provide a calcined catalytic support material.

In the other method, the catalytic support material is prepared by: (1) admixing said borosilicate in a finely-divided state with a hydrosol, sol, or hydrogen of said inorganic oxide in order to uniformly disperse said borosilicate in said hydrosol, sol, or hydrogen of said inorganic oxide to form an admixture; (2) while continually stirring the admixture, adding a gelling medium to promote gellation and to form a gel; (3) drying said gel at a temperature within the range of about 77° F. (25° C.) to about 392° F. (200° C.) for a period of about 10 minutes to about 100 hours in air to form a dried mixture; and (4) calcining said dried mixture at a temperature within the range of about 752° F. (400° C.) to about 1,112° F. (600° C.) for a period of about 20 minutes to about 20 hours to provide a calcined catalytic support material.

The catalytic composition of the present invention can be used for the conversion of hydrocarbon streams. Therefore, there is provided a process for the conversion of a hydrocarbon stream, which process comprises contacting said stream at conversion conditions with the catalytic composition of the present invention. More particularly, there is provided a process for the catalytic isomerization of a xylene feed, which process comprises contacting said feed at isomerization conditions with the catalytic composition of the present invention. Suitable isomerization conditions are listed hereinabove.

Accordingly, there is provided a process for the conversion of a hydrocarbon stream, which process comprises contacting said stream at conversion conditions with a catalytic composition comprising a crystalline borosilicate and a porous refractory inorganic oxide, said borosilicate and said inorganic oxide having been intimately admixed with one another, said borosilicate comprising a molecular sieve material having the following composition in terms of mole ratios of oxides:

$$0.9 \pm 0.2 M_{2/n}O:B_2O_3:YSiO_2:ZH_2O$$

wherein M is at least one cation having a valence of n, Y is between 4 and about 600, and Z is between 0 and about 160.

In another embodiment of the process of the present invention, there is provided a process for the conversion of a hydrocarbon stream, which process comprises contacting said stream at conversion conditions with a catalytic composition comprising at least one catalytically-active metal and a catalytic support comprising a crystalline borosilicate suspended in and distributed throughout a matrix of a refractory inorganic oxide, which composition has been prepared by the method which comprises: (1) admixing said borosilicate in a finely-divided state with a hydrosol, sol, or hydrogel of said inorganic oxide in order to uniformly disperse said borosilicate in said hydrosol, sol, or hydrogel of said inorganic oxide to form an admixture, said borosilicate comprising a molecular sieve material having the following composition in terms of mole ratios of oxides:

$$0.9 \pm 0.2 M_{2/n}O:B_2O_3:YSiO_2:ZH_2O$$

wherein M is at least one cation, n is the valence of the cation, Y is a value within the range of 4 to about 600, and Z is a value within the range of 0 to about 160; (2) while continually stirring the admixture, adding a gelling medium to promote gellation and to form a gel; (3) drying said gel at a temperature of about 77° F. (25° C.) to about 392° F. (200° C.) for a period of about 10 minutes to about 100 hours in the presence of air to form a dried mixture; (4) calcining said dried mixture by heating said dried mixture in air at a maximum rate of about 200° F. per hour (111° C. per hour) to a calcination temperature within the range of about 752° F. (400° C.) to about 1,112° F. (600° C.) and maintaining said dried material at said calcination temperature for a period of about 30 minutes to about 20 hours to provide a calcined catalytic support material; (5) impregnating said calcined catalytic support material with a solution of a heat-decomposable compound of said catalytically-active metal to provide an impregnated material; (6) drying said impregnated material at a temperature of about 77° F. (25° C.) to about 392° F. (200° C.) for a period of about 10 minutes to about 100 hours in air to obtain a dried impregnated material; and (7) calcining said dried impregnated material by heating said dried impregnated material in air at a maximum rate of about 200° F. per hour (111° C. per hour) to a calcination temperature within the range of about 752° F. (400° C.) to about 1,112° F. (600° C.) and maintaining said dried impregnated material at said calcination temperature for a period of about 30 minutes to about 20 hours to provide said catalytic composition.

There is also provided a process for the catalytic isomerization of a xylene feed, which process comprises contacting said feed at isomerization conditions with a catalytic composition comprising a crystalline borosilicate and a porous refractory inorganic oxide, said borosilicate and said inorganic oxide having been intimately admixed with one another, said borosilicate comprising a molecular sieve material having the following composition in terms of mole ratios of oxides:

$$0.9 \pm 0.2 M_{2/n}O:B_2O_3:YSiO_2:ZH_2O$$

wherein M is at least one cation having a valence of n, Y is between 4 and about 600, and Z is between 0 and about 160.

Another embodiment of a process of the present invention is a process for the catalytic isomerization of a xylene feed, which process comprises contacting said feed at isomerization conditions with a catalytic composition comprising at least one catalytically-active metal and a catalytic support comprising a crystalline borosilicate suspended in and distributed throughout a matrix of a refractory inorganic oxide, which composition has been prepared by the method which comprises: (1) admixing said borosilicate in a finely-divided state with a hydrosol, sol, or hydrogel of said inorganic oxide in order to uniformly disperse said borosilicate in said hydrosol, sol, or hydrogel of said inorganic oxide to form an admixture, said borosilicate comprising a molecular sieve material having the following composition in terms of mole ratios of oxides:

$$0.9 \pm 0.2 M_{2/n}O:B_2O_3:YSiO_2:ZH_2O$$

wherein M is at least one cation, n is the valence of the cation, Y is a value within the range of 4 to about 600, and Z is a value within the range of 0 to about 160; (2) while continually stirring the admixture, adding a gelling medium to promote gellation and to form a gel; (3) drying said gel at a temperature of about 77° F. (25° C.) to about 392° F. (200° C.) for a period of about 10 minutes to about 100 hours in the presence of air to form a dried mixture; (4) calcining said dried mixture by heating said dried mixture in air at a maximum rate of about 200° F. per hour (111° C. per hour) to a calcination temperature within the range of about 752° F. (400° C) to about 1,112° F. (600° C.) and maintaining said dried material at said calcination temperature for a period of about 30 minutes to about 20 hours to provide a calcined catalytic support material; (5) impregnating said calcined catalytic support material with a solution of a heat-decomposable compound of said catalytically-active metal to provide an impregnated material; (6) drying said impregnated material at a temperature of about 77° F. (25° C.) to about 392° F. (200° C.) for a period of about 10 minutes to about 100 hours in air to obtain a dried impregnated material; and (7) calcining said dried impregnated material by heating said dried impregnated material in air at a maximum rate of about 200° F. per hour (111° C. per hour) to a calcination temperature within the range of about 752° F. (400° C.) to about 1,112° F. (600° C.) and maintaining said dried impregnated material at said calcination temperature for a period of about 30 minutes to about 20 hours to provide said catalytic composition.

The following examples are presented to facilitate an understanding of the present invention. They are presented for the purpose of illustration only and are not intended to limited the scope of the present invention.

EXAMPLE I

The AMS-1B crystalline borosilicate was prepared by dissolving 0.25 gm of $H_3BO_3$ and 1.6 gm of NaOH in 60 gm of distilled $H_2O$. Then 9.4 gms of tetra-n-propylammonium bromide (TPAB) were added and again dissolved. Finally, 12.7 gm of Ludox AS-30 (30% solids) were added with vigorous stirring. The addition of Ludox gave a curdy, gelatinous, milky solution. This solution was placed in a crystallization vessel and sealed. The vessel was placed in a 329° F. (165° C.) oven and left there for 7 days. At the end of this time, it was opened and its contents were filtered. The recovered crystalline material was washed with copious quantities of $H_2O$ and was then dried at 329° F. (165° C.) in a forced air oven. The dried material was identified by X-ray diffraction as a crystalline material having the typical AMS-1B pattern with 100% crystallinity. Its X-ray diffraction pattern is reported in Table III above. The yield was approximately 2 grams.

EXAMPLE II

In this example, the AMS-1B crystalline borosilicate of Example I was used to produce a catalyst having isomerization capabilities.

The material from Example I was calcined at 1,100° F. (593° C.) in air for 4 hours to remove the organic base. The calcined sieve was exchanged one time with a solution of 20 gm of $NH_4NO_3$ in 200 ml of $H_2O$ and then a second time with 20 gm of ammonium acetate in 200 ml of $H_2O$ at 190° F. (88° C.) for 2 hours. The exchanged borosilicate was dried and calcined in air by heating it to 900° F. (482° C.) in 4 hours, maintaining the borosilicate at 900° F. (482° C.) for 4 hours, and then cooling to 100° F. (38° C.) in 4 hours. The calcined material was exchanged with 100 ml of a 5% Ni($NO_3)_2.6H_2O$ solution for 2 hours at 190° F. (88° C.). The sieve was washed with $H_2O$ and the Ni($NO_3)_2$ solution was apparently washed from the sieve. The sieve was dried and calcined again using the above procedure. About 2 grams of the borosilicate were dispersed in 16.9 gm of PHF-$Al_2O_3$ (a gamma-alumina) hydrosol (8.9% solids) and mixed thoroughly. One ml of distilled $H_2O$ and 1 ml of concentrated $NH_4OH$ were mixed and added to the slurry with intensive mixing. The AMS-1B-$Al_2O_3$ mix was placed in a drying oven at 329° F. (165° C.) for 4 hours. The dried material was again calcined, using the above procedure. The calcined catalyst was crushed to a 30-to-50-mesh material, i.e., material that would pass through a 30-mesh screen (U.S. Sieve Series), but be retained on a 50-mesh screen (U.S. Sieve Series), and impregnated with 2 ml of a solution of 5% Ni($NO_3)_2.6H_2O$ in distilled $H_2O$. The catalyst was again dried and activated by a fourth programmed calcination.

The calcined catalyst contained 65 weight percent borosilicate and 35 weight percent amorphous alumina with approxmately 0.5 weight percent of the total solid as nickel. This material was analyzed by X-ray diffraction and the results are reported in Table I above. The amorphous alumina did not significantly alter the diffraction pattern generated.

One gram of the sized and activated catalyst, identified hereinafter as Catalyst A, was placed in the microreactor and sulfided with $H_2S$ for 20 minutes at room temperature. The catalyst was then placed under H₂ pressure and heated to 600° F. (316° C.). After 1 hour, feed was passed through the microreactor under the following once-through conditions:

| | |
|---|---|
| Temperature | 800° F. (427° C.) |
| Pressure | 150 psig (1,138 KPa) |
| WHSV | 6.28 hrs.$^{-1}$ |
| H/HC, mole ratio | 7 |

The liquid feed and effluent streams for this operation are shown below. Because of the equipment limitations on the screening unit, analyses on liquid streams only were performed and reported. The light-end production over this catalyst was low from the gas chromatographic analysis made on the off-gas stream from the unit. The volume of off-gas was determined to not substantially reduce overall liquid yields over the catalyst.

| Component | Liquid Feed, wt. % | Liquid Product, wt. % |
|---|---|---|
| Paraffins and naphthenes | 0.03 | 0.08 |
| Benzene | — | 1.51 |
| Toluene | 0.077 | 0.26 |
| Ethylbenzene | 19.71 | 17.35 |
| para-Xylene | — | 19.43 |
| meta-Xylene | 79.80 | 46.40 |
| ortho-Xylene | 0.38 | 14.96 |
| C₉⁺* | — | 1.* |

*Approximate values only.

In addition, more detailed and comprehensive analyses of the products were obtained. These are presented hereinbelow in Table IX. The hours on oil for each sample were the sum total of hours from the beginning of the test to the end of the period during which the sample was taken. The term "PATE" represents "percent approach to equilibrium," which has been calculated for each xylene isomer.

TABLE IX

XYLENE ISOMERIZATION WITH CATALYST A TEST NO. 1

| Sample No. | Feed | 3 | 4 | 5 |
|---|---|---|---|---|
| Reactor Temp., °F. | | 640 | 680 | 720 |
| °C. | | 338 | 360 | 382 |
| Reactor Press., psig | | 150 | 150 | 150 |
| KPa | | 1,138 | 1,138 | 1,138 |
| H₂ Flow, ft³/hr | | 0.3 | 0.3 | 0.3 |
| m³/hr | | 0.009 | 0.009 | 0.009 |
| Feed Rate, gm/hr | | 7.48 | 8.53 | 9.14 |
| Product Analysis, wt. % | | | | |
| Paraffins + Naphthenes | — | 0.066 | 0.33 | 0.17 |
| Benzene | — | 0.107 | 0.28 | 0.58 |
| Toluene | 0.03 | 0.154 | 0.26 | 0.20 |
| Ethylbenzene (EB) | 20.97 | 20.30 | 19.94 | 19.58 |
| p-Xylene (pX) | — | 11.38 | 14.31 | 18.45 |
| m-Xylene (mX) | 78.5 | 62.49 | 57.60 | 50.57 |
| o-Xylene (oX) | — | 5.44 | 7.28 | 10.46 |
| C₉⁺ | 0.5 | — | — | — |
| Calculated Results | | | | |
| ppH₂, psia | | 140.5 | 137.7 | 136.1 |
| H/HC | | 5.8 | 5.1 | 4.8 |
| Contact Time, Sec | | 3.03 | 2.87 | 2.74 |
| WHSV, hr⁻¹ | | 7.48 | 8.53 | 9.14 |
| pX PATE, % | | 60.5 | 76.4 | 98.4 |
| mX PATE, % | | 44.6 | 57.4 | 76.5 |
| oX PATE, % | | 28.16 | 37.9 | 54.4 |
| EB Conversion, % | | 3.2 | 4.9 | 6.6 |
| Time on Oil, hrs | | 16.5 | 22.5 | 40.5 |
| Sample No. | 6 | 9 | 10 | 11 |
| Reactor Temp., °F. | 760 | 800 | 800 | 800 |
| °C. | 404 | 427 | 427 | 427 |
| Reactor Press., psig | 150 | 150 | 150 | 150 |
| KPa | 1,138 | 1,138 | 1,138 | 1,138 |
| H₂ Flow, ft³/hr | 0.3 | 0.3 | 0.3 | 0.3 |
| m³/hr | 0.009 | 0.009 | 0.009 | 0.009 |
| Feed Rate, gm/hr | 8.58 | 6.28 | 8.20 | 5.47 |
| Product Analysis, wt. % | | | | |
| Paraffins + Naphthenes | — | 0.09 | 0.12 | — |
| Benzene | 0.90 | 1.79 | 1.55 | 1.64 |
| Toluene | 0.24 | 0.31 | 0.25 | 0.28 |
| Ethylbenzene (EB) | 19.1 | 17.9 | 18.3 | 18.1 |
| p-Xylene (pX) | 19.2 | 20.8 | 20.2 | 20.7 |
| m-Xylene (mX) | 49.0 | 44.2 | 45.9 | 45.0 |
| o-Xylene (oX) | 11.5 | 14.9 | 13.7 | 14.3 |
| C₉⁺ | — | — | — | — |
| Calculated Results | | | | |
| ppH₂, psia | 137.6 | 143.9 | 138.6 | 146.3 |
| H/HC | 5.1 | 6.9 | 5.3 | 8.0 |
| Contact Time, Sec | 2.68 | 2.71 | 2.61 | 2.76 |
| WHSV, hr⁻¹ | 8.58 | 6.28 | 8.20 | 5.47 |
| pX PATE, % | 102.5 | 111.06 | 108.0 | 110.4 |
| mX PATE, % | 80.7 | 93.3 | 88.6 | 91.3 |
| oX PATE, % | 59.0 | 75.9 | 69.7 | 72.7 |
| EB Conversion, % | 8.9 | 14.6 | 12.7 | 13.7 |
| Time on Oil, hrs | 47.5 | 136.5 | 145.6 | 160.5 |
| Sample No. | 12 | 13 | 16 | 17 |
| Reactor Temp., °F. | 800 | 800 | 801 | 801 |
| °C. | 427 | 427 | 428 | 428 |
| Reactor Press., psig | 150 | 150 | 150 | 150 |
| KPa | 1,138 | 1,138 | 1,138 | 1,138 |
| H₂ Flow, ft³/hr | 0.3 | 0.3 | 0.3 | 0.3 |
| m³/hr | 0.009 | 0.009 | 0.009 | 0.009 |
| Feed Rate, gm/hr | 5.53 | 6.23 | 6.71 | 6.19 |
| Product Analysis, wt. % | | | | |
| Paraffins + Naphthenes | 0.06 | 0.09 | 0.06 | 0.07 |
| Benzene | 3.09 | 3.00 | 1.61 | 1.33 |
| Toluene | 0.48 | 0.46 | 0.25 | 0.20 |
| Ethylbenzene (EB) | 16.4 | 16.4 | 17.1 | 17.6 |
| p-Xylene (pX) | 21.0 | 21.1 | 19.2 | 14.5 |
| m-Xylene (mX) | 42.4 | 42.4 | 45.5 | 51.3 |
| o-Xylene (oX) | 16.6 | 16.5 | 15.2 | 14.2 |
| C₉⁺ | — | — | 1.18 | 0.80 |
| Calculated Results | | | | |
| ppH₂, psia | 146.1 | 144.1 | 144.2 | 144.2 |
| H/HC | 7.9 | 7.0 | 7.0 | 7.0 |
| Contact Time, Sec | 2.75 | 2.71 | 2.72 | 2.72 |
| WHSV, hr⁻¹ | 5.53 | 6.23 | 6.71 | 6.19 |
| pX PATE, % | 111.6 | 112.5 | 102.6 | 76.8 |
| mX PATE, % | 98.2 | 98.2 | 89.7 | 74.4 |
| oX PATE, % | 84.7 | 84.1 | 77.2 | 72.2 |
| EB Conversion, % | 21.8 | 21.8 | 18.5 | 16.1 |
| Time on Oil, hrs | 168.5 | 184.5 | 223.0 | 238.5 |
| Sample No. | 18 | 19 | 20 | 21 |
| Reactor Temp., °F. | 724 | 721 | 800 | 801 |
| °C. | 384 | 383 | 427 | 428 |
| Reactor Press., psig | 150 | 150 | 150 | 150 |
| KPa | 1,138 | 1,138 | 1,138 | 1,138 |
| H₂ Flow, ft³/hr | 0.3 | 0.3 | 0.3 | 0.3 |
| m³/hr | 0.009 | 0.009 | 0.009 | 0.009 |
| Feed Rate, gm/hr | 6.29 | 4.88 | 6.63 | 5.00 |
| Product Analysis, wt. % | | | | |
| Paraffins + Naphthenes | 0.05 | 0.07 | 0.14 | 0.06 |
| Benzene | 0.52 | 0.70 | 1.45 | 1.87 |
| Toluene | 0.13 | 0.16 | 0.22 | 0.31 |
| Ethylbenzene (EB) | 19.3 | 18.8 | 17.8 | 17.1 |
| p-Xylene (pX) | 16.3 | 17.8 | 18.5 | 19.3 |
| m-Xylene (mX) | 52.7 | 49.4 | 46.8 | 44.3 |
| o-Xylene (oX) | 10.4 | 12.3 | 14.2 | 16.0 |
| C₉⁺ | 0.60 | 0.66 | 0.90 | 1.08 |
| Calculated Results | | | | |
| ppH₂, psia | 143.9 | 147.1 | 142.9 | 147.7 |
| H/HC | 6.9 | 8.4 | 6.6 | 8.7 |
| Contact Time, Sec | 2.89 | 2.96 | 2.69 | 2.78 |
| WHSV, hr⁻¹ | 6.29 | 4.88 | 6.63 | 5.00 |
| pX PATE, % | 86.6 | 94.9 | 99.1 | 103.4 |
| mX PATE, % | 70.3 | 79.5 | 85.6 | 92.6 |
| oX PATE, % | 54.1 | 64.1 | 72.5 | 81.9 |
| EB Conversion, % | 8.0 | 10.3 | 15.1 | 18.5 |

TABLE IX-continued

XYLENE ISOMERIZATION WITH CATALYST A
TEST NO. 1

| Time on Oil, hrs | 245.5 | 309.0 | 317.01 | 333.0 |
|---|---|---|---|---|

EXAMPLE III

In this example, another AMS-1B borosilicate was prepared. A solution was prepared by dissolving 2.5 gm of $H_3BO_3$ and 7.5 gm of NaOH in 600 gm of distilled water. Then 94.3 gm of tetrapropylammonium bromide was dissolved in the solution. To the solution was added 114.5 gm of Ludox HS-30 and the resulting mixture was thoroughly blended. It was subsequently transferred to a 1-liter crystallizer. Crystallization was carried out at a temperature of 329° F. (165° C.) and a pressure of about 105 psig (827 KPa) for 7 days. The solid material was filtered from the crystallization solution and washed with approximately 1 liter of distilled water. The wash material was dried in a forced draft drying oven at a temperature of 329° F. (165° C.) overnight (approximately 16 hours). The dried material, which weighed 35.6 gm, was transferred to a calcining furnace, where it was calcined at a temperature of 1,000° F. (538° C.) for 4 hours after it had been heated for 4.5 hours such that the temperature increased at a rate of 200° F. per hour (111° C. per hour) to the 1,000° F. (538° C.)

A 20-gm portion of the calcined material, identified as crystalline AMS-1B borosilicate by its X-ray diffraction pattern, was slurried in a solution that had been prepared by dissolving 30 gm of ammonium acetate in 300 gm of distilled water. This ammonium cation-exchange was carried out for 1.5 hrs at a temperature of 194° F. (90° C.). After this exchange had been completed, the borosilicate was filtered from the solution and washed with 150 ml of distilled water. The exchange procedure was repeated 4 times. After the last exchange and subsequent wash, the borosilicate was filter dried and then transferred to a calcining furnace. The furnace was held at a temperature of 250° F. (121° C.) for 3 hrs before the borosilicate was calcined under a temperature control program at a temperature of 900° F. (482° C.) for 4 hrs. During the program, 3.25 hrs were used to increase the temperature in a linear manner from 250° F. (121° C.) to a temperature of 900° F. (482° C.). The furnace was held at a temperature of 900° F. (482° C.) for 4 hrs, and a minimum of 3.25 hrs was required to cool the material from 900° F. (482° C.) to a temperature of 250° F. (121° C.). The calcined material was the hydrogen form of the borosilicate.

The resulting hydrogen form of the borosilicate was subsequently exchanged with a nickel nitrate solution. For this latter cation exchange, 150 ml of a 5% solution was employed. The exchange was carried out at a temperature of 194° F. (90° C.) for a period of 1.5 hrs. The solution was prepared by dissolving 7.5 gm of $Ni(NO_3)_2.6H_2O$ in distilled water. The exchanged borosilicate was filtered from the exchange solution, washed with 150 ml of distilled water, and filter dried. The material was then dried at a temperature of 329° F. (165° C.) for 3 hrs in a forced draft drying oven and then calcined according to the above-described program at a temperature of 900° F. (482° C.) for 4 hrs. The resultant borosilicate was then in the nickel- and hydrogen-form and weighed 19.2 gm.

A catalyst support was prepared by thoroughly dispersing the above nickel- and hydrogen-form of borosilicate in 118.7 gm of a PHF-alumina hydrosol (8.7% solids), which hydrosol was obtained from the American Cyanamid Company. The hydrosol-borosilicate blend was subsequently gelled by adding a solution that had been prepared by mixing 7.5 ml of concentrated ammonium hydroxide and 7.5 ml of distilled water. The resulting gel was dried for 4 hrs at a temperature of 329° F. (165° C.) in the forced draft drying oven. The sol was then transferred to the drying oven, which was maintained at a temperature of 250° F. (121° C.) for 3 hrs and then subjected to a programmed calcination, as described hereinabove. The calcined material was pulverized and sieved to obtain a 30-to-50-mesh material (U.S. Sieve Series), i.e., material that would pass through a 30-mesh screen (U.S. Sieve Series) but be retained upon a 50-mesh screen (U.S. Sieve Series). This 30-to-50-mesh material was impregnated with 11.5 ml of a 5% $Ni(NO_3)_2.6H_2O$ solution, which had been prepared by dissolving the $Ni(NO_3)_2.6H_2O$ in sufficient distilled water. The resulting impregnated material was subjected to a final calcination with a 900° F. (482° C.) calcination program, but the material was dried for a period of 5 hrs at a temperature of 250° F. (121° C.), rather than at a period of 3 hrs for such drying. As the material was being dried at the temperature of 250° F. (121° C.), it was stirred frequently to facilitate an even drying. The finished catalyst, i.e., the calcined catalyst, is hereinafter identified as Catalyst B.

The activated Catalyst B was tested for its ability to isomerize xylenes. A 1-gm portion of the activated Catalyst B was placed in a microreactor and sulfided with pure $H_2S$ for 15 minutes at room temperature. The flow rate of $H_2S$ was approximately 0.3 ft$^3$/hr (0.009 m$^3$/hr). The catalyst was then placed under $H_2$ pressure and heated to a temperature of 800° F. (427° C.). After 1 hr, a synthetic xylene isomerization feed was passed through the microreactor under the conditions specified in the following Table X. The test results obtained from this test, Test No. 2, are presented hereinbelow in Table X. The results obtained for this test were obtained from Analytical Services. The time on oil for a particular sample is a sum of the hours on oil including the complete amount of time during which that particular sample was taken.

TABLE X

XYLENE ISOMERIZATION WITH CATALYST B
TEST NO. 2

| Sample No. | Feed | 2 | 3 |
|---|---|---|---|
| Reactor Temp., °F. | | 800 | 840 |
| °C. | | 427 | 449 |
| Reactor Press., psig | | 150 | 150 |
| KPa | | 1,138 | 1,138 |
| $H_2$ Rate, ft$^3$/hr | | 0.3 | 0.3 |
| m$^3$/hr | | 0.009 | 0.009 |
| Feed Rate, gm/hr | | 7.80 | 6.28 |
| Product Analysis, wt. % | | | |
| Paraffins + Naphthenes | 0.05 | 0.12 | 0.10 |
| Benzene | — | 1.28 | 2.76 |
| Toluene | 0.07 | 0.28 | 0.51 |
| Ethylbenzene (EB) | 19.56 | 16.92 | 14.88 |
| p-Xylene (pX) | 8.65 | 16.40 | 18.45 |
| m-Xylene (mX) | 47.83 | 42.87 | 41.74 |
| o-Xylene (oX) | 23.66 | 21.21 | 20.13 |
| $C_9^+$ | 0.22 | 0.92 | 1.43 |
| Diethylbenzene | — | 0.40 | 0.59 |
| Calculated Results | | | |
| pp$H_2$, psia | | 136.8 | 141.5 |
| H/HC | | 4.9 | 6.1 |
| Contact Time, Sec | | 2.58 | 2.58 |
| WHSV, hr$^{-1}$ | | 7.80 | 6.28 |
| pX PATE, % | | 75.8 | 96.8 |

TABLE X-continued

| XYLENE ISOMERIZATION WITH CATALYST B TEST NO. 2 | | |
|---|---|---|
| mX PATE, % | 84.9 | 99.4 |
| oX PATE, % | 62.1 | 92.7 |
| EB Conversion, % | 13.5 | 23.9 |
| Time on Oil, hrs | 23.0 | 38.7 |

| Sample No. | 4 | 5 | 6 |
|---|---|---|---|
| Reactor Temp., °F. | 840 | 840 | 800 |
| °C. | 449 | 449 | 427 |
| Reactor Press., psig | 150 | 150 | 150 |
| KPa | 1,138 | 1,138 | 1,138 |
| H$_2$ Rate, ft$^3$/hr | 0.3 | 0.3 | 0.3 |
| m$^3$/hr | 0.009 | 0.009 | 0.009 |
| Feed Rate, gm/hr | 7.62 | 9.91 | 6.67 |
| Product Analysis, wt. % | | | |
| Paraffins + Naphthenes | 0.04 | 0.02 | 0.02 |
| Benzene | 2.42 | 2.59 | 1.42 |
| Toluene | 0.51 | 0.46 | 0.23 |
| Ethylbenzene (EB) | 15.14 | 14.68 | 16.62 |
| p-Xylene (pX) | 18.35 | 18.42 | 16.99 |
| m-Xylene (mX) | 41.60 | 41.49 | 42.28 |
| o-Xylene (oX) | 20.31 | 20.21 | 21.11 |
| C$_9$+ | 1.61 | 2.11 | 1.33 |
| Diethylbenzene | 0.72 | 1.04 | 0.80 |
| Calculated Results | | | |
| ppH$_2$, psia | 137.4 | 130.8 | 140.3 |
| H/HC | 5.0 | 3.9 | 5.7 |
| Contact Time, Sec | 2.51 | 2.39 | 2.64 |
| WHSV, hr$^{-1}$ | 7.62 | 9.91 | 6.67 |
| pX PATE, % | 96.0 | 97.00 | 81.8 |
| mX PATE, % | 101.2 | 101.8 | 93.8 |
| oX PATE, % | 87.6 | 89.3 | 63.9 |
| EB Conversion, % | 22.6 | 24.9 | 15.0 |
| Time on Oil, hrs | 44.0 | 60.5 | 67.5 |

| Sample No. | 7 | 8 | 9 |
|---|---|---|---|
| Reactor Temp., °F. | 800 | 800 | 800 |
| °C. | 427 | 427 | 427 |
| Reactor Press., psig | 150 | 150 | 150 |
| KPa | 1,138 | 1,138 | 1,138 |
| H$_2$ Rate, ft$^3$/hr | 0.3 | 0.3 | 0.3 |
| m$^3$/hr | 0.009 | 0.009 | 0.009 |
| Feed Rate, gm/hr | 5.61 | 5.37 | 5.08 |
| Product Analysis, wt. % | | | |
| Paraffins + Naphthenes | 0.03 | 0.03 | 0.02 |
| Benzene | 1.38 | 1.30 | 1.29 |
| Toluene | 0.21 | 0.20 | 0.20 |
| Ethylbenzene (EB) | 16.63 | 16.71 | 16.78 |
| p-Xylene (pX) | 17.46 | 17.30 | 17.38 |
| m-Xylene (mX) | 42.12 | 42.20 | 42.09 |
| o-Xylene (oX) | 20.99 | 21.19 | 21.15 |
| C$_9$+ | 1.18 | 1.07 | 1.09 |
| Diethylbenzene | 0.74 | 0.68 | 0.68 |
| Calculated Results | | | |
| ppH$_2$, psia | 143.6 | 144.4 | 145.4 |
| H/HC | 6.8 | 7.1 | 7.5 |
| Contact Time, Sec | 2.71 | 2.72 | 2.74 |
| WHSV, hr$^{-1}$ | 5.61 | 5.37 | 5.08 |
| pX PATE, % | 86.0 | 84.2 | 85.1 |
| mX PATE, % | 98.1 | 97.8 | 99.0 |
| oX PATE, % | 68.0 | 63.9 | 64.5 |
| EB Conversion, % | 15.0 | 14.6 | 14.2 |
| Time on Oil, hrs | 82.75 | 90.25 | 107.5 |

EXAMPLE IV

Another AMS-1B borosilicate was prepared. The following quantities of chemicals were employed in its preparation: 1,800.0 gm of distilled water; 120.0 gm of H$_3$BO$_3$; 57.0 gm of NaOH; 282.9 gm of tetrapropylammonium bromide; 228.0 gm of Ludox HS-40. The resulting pH of the slurry was 10.6. The borosilicate was crystallized at a temperature of 329° F. (165° C.) for 7 days. The crystallized borosilicate was then treated as described hereinabove in Example III. After drying, 92.3 gm of the crystalline borosilicate were recovered. The calcined borosilicate was identified by X-ray diffraction analysis as an AMS-1B borosilicate. It was then introduced into a catalytic composition in a manner similar to that as described in Example III for the preparation of Catalyst B. However, several exceptions to the method of preparation in Example III were employed. These exceptions were: (1) a 50-gm portion of borosilicate was used with 100 gm of ammonium acetate for each exchange; (2) a 15-gm portion of the exchanged and calcined hydrogen-form crystalline borosilicate was exchanged with 150 ml of the 5% solution of Ni(NO$_3$)$_2$.6H$_2$O; and (3) a 14.3-gm portion of nickel- and hydrogen-form crystalline borosilicate was dispersed in 88.5 gm of PHF-alumina hydrosol obtained from the American Cyanamid Company. The finished catalyst is hereinafter identified as Catalyst C.

A 1-gm sample of Catalyst C was tested for xylene isomerization as discussed hereinabove in Examples II and III. The results of this test, Test No. 3, are presented hereinafter in Table XI.

TABLE XI

| | | XYLENE ISOMERIZATION WITH CATALYST C TEST NO. 3 | | | | | | | |
|---|---|---|---|---|---|---|---|---|---|
| Sample No. | Feed | 1 | 3 | 5 | 6 | 7 | 8 | 9 |
| Reactor Temp., °F. | | 680 | 680 | 720 | 720 | 760 | 800 | 840 |
| °C. | | 360 | 360 | 382 | 382 | 404 | 427 | 449 |
| Reactor Press., psig | | 150 | 150 | 150 | 150 | 150 | 150 | 150 |
| KPa | | 1,138 | 1,138 | 1,138 | 1,138 | 1,138 | 1,138 | 1,138 |
| H$_2$ Rate, ft$^3$/hr | | 0.3 | 0.3 | 0.3 | 0.3 | 0.3 | 0.3 | 0.3 |
| m$^3$/hr | | 0.009 | 0.009 | 0.009 | 0.009 | 0.009 | 0.009 | 0.009 |
| Feed Rate, gm/hr | | 2.59 | 4.25 | 6.29 | 6.40 | 5.93 | 5.57 | 5.81 |
| Product Analysis, wt. % | | | | | | | | |
| Paraffins + Naphthenes | 0.05 | — | — | — | 0.01 | 0.01 | 0.02 | 0.02 |
| Benzene | — | 0.30 | 0.22 | 0.36 | 0.34 | 0.58 | 0.96 | 1.65 |
| Toluene | 0.07 | 0.15 | 0.14 | 0.15 | 0.16 | 0.23 | 0.32 | 0.52 |
| Ethylbenzene (EB) | 19.56 | 18.82 | 19.01 | 18.83 | 18.80 | 18.23 | 17.66 | 16.33 |
| p-Xylene (pX) | 8.65 | 16.49 | 15.71 | 16.48 | 15.77 | 17.99 | 18.46 | 18.71 |
| m-Xylene (mX) | 47.83 | 43.77 | 44.06 | 43.55 | 43.89 | 42.60 | 42.25 | 41.63 |
| o-Xylene (oX) | 23.66 | 20.47 | 20.81 | 20.63 | 20.57 | 19.38 | 18.77 | 18.42 |
| C$_9$+ | 0.22 | — | — | — | 0.46 | 0.99 | 1.54 | 2.71 |
| Diethylbenzene | — | — | — | — | 0.10 | 0.19 | 0.29 | 0.47 |
| Calculated Results | | | | | | | | |
| ppH$_2$, psia | | 154.3 | 143.5 | 141.4 | 141.0 | 142.6 | 143.7 | 143.0 |
| H/HC | | 14.8 | 6.8 | 6.1 | 5.9 | 6.5 | 6.8 | 6.6 |
| Contact Time, Sec | | 3.21 | 2.99 | 2.85 | 2.84 | 2.77 | 2.71 | 2.61 |

TABLE XI-continued

| | | XYLENE ISOMERIZATION WITH CATALYST C TEST NO. 3 | | | | | | |
|---|---|---|---|---|---|---|---|---|
| Sample No. | Feed | 1 | 3 | 5 | 6 | 7 | 8 | 9 |
| WHSV, hr$^{-1}$ | | 1.45 | 4.25 | 6.29 | 6.40 | 5.93 | 5.57 | 5.81 |
| pX PATE, % | | 74.8 | 67.9 | 75.3 | 69.5 | 92.0 | 98.24 | 103.1 |
| mX PATE, % | | 79.8 | 73.3 | 80.2 | 70.4 | 87.5 | 86.28 | 88.0 |
| oX PATE, % | | 69.0 | 61.5 | 69.1 | 68.2 | 98.0 | 115.86 | 127.5 |
| EB Conversion, % | | 3.8 | 2.8 | 3.7 | 3.9 | 6.8 | 9.7 | 16.5 |
| Time on Oil, hrs | | 16.0 | 40.0 | 64.0 | 71 | 88 | 95 | 112 |

EXAMPLE V

In this example, an impregnated catalytic composition was prepared and tested for its ability to isomerize xylenes. A 2-gm portion of Catalyst C was impregnated with a solution of 5% Ni(NO$_3$)$_2$.6H$_2$O. The solution was prepared as explained hereinabove. Sufficient solution was employed for an adequate impregnation. The impregnated catalyst was dried in a forced draft drying oven at a temperature of 329° F. (165° C.) with frequent agitation. The catalyst was given an additional drying step at a temperature of 482° F. (250° C.) prior to being subjected to a programmed calcination at 900° F. (482° C.). A 1-gm portion of the impregnated and calcined catalyst, identified hereinafter as Catalyst D, was tested for its ability to isomerize xylenes. The test procedure employed in Example II was used. Test results from this test, Test No. 4, are presented in Table XII.

An additional test was made with Catalyst D. This test is identified hereinafter as Test No. 5. Its results are presented hereinafter in Table XIII.

TABLE XII

| | XYLENE ISOMERIZATION WITH CATALYST D TEST NO. 4 | | | | | | | | | |
|---|---|---|---|---|---|---|---|---|---|---|
| Sample No. | Feed | 1 | 2 | 3 | 4 | 5 | 6 | 7 | 8 | 9 |
| Reactor Temp., °F. | | 680 | 680 | 640 | 640 | 720 | 720 | 760 | 800 | 840 |
| °C. | | 360 | 360 | 338 | 338 | 382 | 382 | 404 | 427 | 449 |
| Reactor Press., psig | | 150 | 150 | 150 | 150 | 150 | 150 | 150 | 150 | 150 |
| KPa | | 1,138 | 1,138 | 1,138 | 1,138 | 1,138 | 1,138 | 1,138 | 1,138 | 1,138 |
| H$_2$ Rate, ft$^3$/hr | | 0.3 | 0.3 | 0.3 | 0.3 | 0.3 | 0.3 | 0.3 | 0.3 | 0.3 |
| m$^3$/hr | | 0.009 | 0.009 | 0.009 | 0.009 | 0.009 | 0.009 | 0.009 | 0.009 | 0.009 |
| Feed Rate, gm/hr | | 5.28 | 6.66 | 5.67 | 6.71 | 6.21 | 6.19 | 5.42 | 6.24 | 5.47 |
| Product Analysis, wt. % | | | | | | | | | | |
| Paraffins + Naphthenes | 0.05 | 0.08 | — | — | — | 0.05 | 0.06 | — | — | 0.02 |
| Benzene | — | 0.39 | 0.37 | 0.24 | 0.19 | 0.51 | 0.54 | 0.87 | 1.26 | 2.25 |
| Toluene | 0.07 | 0.42 | 0.24 | 0.16 | 0.14 | 0.24 | 0.24 | 0.35 | 0.49 | 0.78 |
| Ethylbenzene (EB) | 19.56 | 18.87 | 18.80 | 19.12 | 19.10 | 18.40 | 18.37 | 17.64 | 16.75 | 15.21 |
| p-Xylene (pX) | 8.65 | 18.17 | 17.93 | 16.39 | 16.08 | 18.58 | 18.77 | 19.11 | 19.20 | 19.08 |
| m-Xylene (mX) | 47.83 | 42.68 | 42.94 | 43.48 | 43.63 | 42.69 | 42.50 | 42.56 | 42.48 | 42.03 |
| o-Xylene (oX) | 23.66 | 19.39 | 19.73 | 20.62 | 20.88 | 18.96 | 18.87 | 18.47 | 18.14 | 18.11 |
| C$_9$+ | 0.22 | — | — | — | — | 0.56 | 0.64 | 1.00 | 1.67 | 2.53 |
| Diethylbenzene | — | — | — | — | — | 0.20 | 0.22 | 0.36 | 0.47 | 0.59 |
| Calculated Results | | | | | | | | | | |
| ppH$_2$, psia | | 144.7 | 140.3 | 143.5 | 140.1 | 141.7 | 141.8 | 144.3 | 141.6 | 144.1 |
| H/HC | | 7.2 | 5.7 | 6.8 | 5.7 | 6.2 | 6.2 | 7.1 | 6.1 | 7.0 |
| Contact Time, Sec | | 3.01 | 2.92 | 3.10 | 3.02 | 2.85 | 2.85 | 2.81 | 2.67 | 2.63 |
| WHSV, hr$^{-1}$ | | 5.28 | 6.66 | 5.63 | 6.68 | 6.21 | 6.19 | 5.42 | 6.24 | 5.47 |
| pX PATE, % | | 92.1 | 88.99 | 73.9 | 70.8 | 96.6 | 98.7 | 102.6 | 104.8 | 105.7 |
| mX PATE, % | | 94.8 | 93.5 | 86.0 | 84.2 | 91.2 | 93.7 | 89.7 | 85.6 | 85.4 |
| oX PATE, % | | 88.8 | 93.6 | 61.3 | 56.7 | 103.2 | 104.6 | 120.0 | 133.2 | 138.4 |
| EB Conversion, % | | 3.5 | 3.9 | 2.2 | 2.3 | 5.9 | 6.1 | 9.8 | 14.4 | 22.2 |
| Time on Oil, hrs | | 16.0 | 23.0 | 40.0 | 47.0 | 64.0 | 71.0 | 88.0 | 95.0 | 112.0 |

TABLE XIII

| | XYLENE ISOMERIZATION WITH CATALYST D TEST NO. 5 | | | | | | | | | |
|---|---|---|---|---|---|---|---|---|---|---|
| Sample No. | Feed | 1 | 2 | 3 | 4 | 5 | 6 | 7 | 8 | 9 |
| Reactor Temp., °F. | | 722 | 720 | 720 | 720 | 760 | 760 | 800 | 800 | 840 |
| °C. | | 383 | 382 | 382 | 382 | 404 | 404 | 427 | 427 | 449 |
| Reactor Press., psig | | 150 | 150 | 150 | 150 | 150 | 150 | 150 | 150 | 150 |
| KPa | | 1,138 | 1,138 | 1,138 | 1,138 | 1,138 | 1,138 | 1,138 | 1,138 | 1,138 |
| H$_2$ Rate, ft$^3$/hr | | 0.3 | 0.3 | 0.3 | 0.3 | 0.3 | 0.3 | 0.3 | 0.3 | 0.3 |
| m$^3$/hr | | 0.009 | 0.009 | 0.009 | 0.009 | 0.009 | 0.009 | 0.009 | 0.009 | 0.009 |
| Feed Rate, gm/hr | | 2.22 | 5.81 | 4.78 | 6.37 | 5.76 | 6.50 | 4.30 | 4.27 | 0.71 |
| Product Analysis, wt. % | | | | | | | | | | |
| Paraffins + Naphthenes | 0.05 | 1.24 | — | 0.02 | 0.03 | 0.01 | 0.02 | 0.01 | 0.01 | 0.01 |
| Benzene | — | 0.77 | 0.67 | 0.65 | 0.64 | 0.86 | 0.93 | 1.29 | 1.54 | 1.45 |
| Toluene | 0.07 | 0.52 | 0.33 | 0.29 | 0.29 | 0.34 | 0.34 | 0.46 | 0.52 | 0.44 |
| Ethylbenzene (EB) | 19.56 | 17.88 | 18.46 | 18.38 | 18.01 | 17.62 | 17.63 | 16.78 | 16.70 | 15.41 |
| p-Xylene (pX) | 8.65 | 18.98 | 19.11 | 18.99 | 19.02 | — | 19.17 | 19.07 | 19.39 | 19.21 |
| m-Xylene (mX) | 47.83 | 42.48 | 42.83 | 42.88 | 42.75 | 79.97 | 42.46 | 42.33 | 42.36 | 42.47 |
| o-Xylene (oX) | 23.66 | 18.14 | 18.60 | 18.79 | 18.07 | — | 18.31 | 18.25 | 17.95 | 18.66 |
| C$_9$+ | 0.22 | — | — | — | — | 1.20 | 1.11 | 1.82 | 1.61 | 2.34 |
| Diethylbenzene | — | — | — | — | — | 0.39 | 0.37 | 0.52 | 0.47 | 0.62 |

TABLE XIII-continued

XYLENE ISOMERIZATION WITH CATALYST D
TEST NO. 5

| Sample No. | Feed | 1 | 2 | 3 | 4 | 5 | 6 | 7 | 8 | 9 |
|---|---|---|---|---|---|---|---|---|---|---|
| Calculated Results | | | | | | | | | | |
| ppH$_2$, psia | | 155.7 | 143.0 | 146.4 | 141.2 | 143.1 | 140.8 | 148.1 | 148.2 | 161.7 |
| H/HC | | 17.3 | 6.6 | 8.0 | 6.0 | 6.6 | 5.9 | 8.9 | 9.0 | 53.7 |
| Contact Time, Sec | | 3.13 | 2.88 | 2.95 | 2.84 | 2.78 | 2.74 | 2.79 | 2.79 | 2.75 |
| WHSV, hr$^{-1}$ | | 2.22 | 5.81 | 4.75 | 6.37 | 5.76 | 6.50 | 4.30 | 4.24 | .71 |
| pX PATE, % | | 102.0 | 101.1 | 99.6 | 100.4 | — | 103.68 | 103.9 | 106.5 | 104.3 |
| mX PATE, % | | 88.8 | 91.6 | 91.9 | 92.1 | — | 89.61 | 86.5 | 85.9 | 88.0 |
| oX PATE, % | | 118.2 | 112.6 | 109.0 | 110.5 | — | 122.5 | 129.6 | 136.9 | 130.7 |
| EB Conversion, % | | 8.6 | 5.6 | 6.0 | 4.9 | 9.9 | 9.9 | 14.2 | 14.6 | 21.2 |
| Time on Oil, hrs | | 16.0 | 23.0 | 40.0 | 47.0 | 64.0 | 71.0 | 88.0 | 95.0 | 112.0 |

The results in Tables XI, XII, and XIII clearly show that the catalytic composition which contains an impregnated hydrogenation metal, Catalyst D, outperforms the catalyst that does not contain any of the impregnated nickel, i.e., Catalyst C.

EXAMPLE VI

Another embodiment of the AMS-1B crystalline borosilicate of the present invention was prepared. This borosilicate was prepared by using the following quantities of chemicals: 11,900.0 gm of distilled water; 275.0 gm of NaOH; 430.0 gm of H$_3$BO$_3$; 1,755.0 gm of tetrapropylammonium bromide; and 1,623.0 gm of Ludox HS-40. Two batches of this material were prepared. Each batch was made from the above quantities of ingredients. The first batch had a pH of 10.61, while the second batch had a pH of 10.76.

In the case of each batch, five identical portions, each of which would fit into a 1-gallon Waring Blendor, were prepared. Then the five portions were added to a 5-gallon stirred autoclave for a 7-day crystallization at a temperature of 329° F. (165° C.). Stirring in the autoclave was maintained at a rate of 250 rpm. Each batch of the crystallized material was washed from the crystallizer, filtered from the crystallization solution, and washed with 5 liters of distilled water. The resultant borosilicates were then dried and program calcined at 1,000° F. (538° C.) as described in Example III. The crystalline material, in each case, was identified by X-ray diffraction patterns as being AMS-1B crystalline borosilicate molecular sieves.

A 200-gm portion of each sieve was cation-exchanged to the hydrogen form of the borosilicate by employing ammonium acetate cation exchange. Each 200-gm sample was split into two 100-gm samples for ease of cation-exchanging. Each 100-gm quantity of crystalline borosilicate was slurry-exchanged with 200 gm of ammonium acetate that had been dissolved in 1,500 ml of distilled water at a temperature of 203° F. (95° C.) for a period of 2 hours. The crystalline material was filtered from the exchange solution, washed with approximately 200 ml of distilled water, and filter dried for 2 hours. The dried filter cake was again exchanged according to the above-described exchange technique. After the second exchange, the crystalline material was washed with approximately 4 liters of distilled water and filter dried. This air-dried solid was then program calcined at a temperature of 1,000° F. (538° C.) for 12 hours. The two 100-gm samples from each batch of crystalline borosilicate were blended and the blended material constituted a hydrogen-form of ASM-1B crystalline borosilicate. The blend of the first two 100-gm samples is identified hereinafter as Borosilicate No. 4, while the blend of the second two 100-gm samples is identified hereinafter as Borosilicate No. 5.

EXAMPLE VII

In this example, 15 gm of Borosilicate No. 4 were dispersed in 167 mg of PHF-alumina hydrosol (8.7% solids) which had been obtained from the American Cyanamid Company. The mixture was thoroughly blended in a Waring Blendor. Twelve milliliters of a 1:1 solution of concentrated ammonium hydroxide and distilled water were rapidly added to the blended slurry while the blender was being operated at a high speed for two minutes. The resulting gelled solid was transferred to a forced draft drying oven to dry for 16 hours at a temperature of 329° F. (165° C.). The dried solid was then program calcined at a temperature of 1,000° F. (538° C.) to provide a catalyst which was made up of 50 wt.% Borosilicate No. 4 and 50 wt.% gamma-alumina. This catalyst is identified hereinafter as Catalyst E.

EXAMPLE VIII

A catalyst, identified hereinafter as Catalyst F, was prepared with Borosilicate No. 5. The preparation was identical to that of Catalyst E described hereinabove in Example VII.

EXAMPLE IX

A number of additional catalytic compositions were prepared, which catalytic compositions employed as starting materials either Borosilicate No. 4 or Borosilicate No. 5. Each of these catalysts was prepared according to the following procedure.

In the case of metal-cation-exchanged samples, the hydrogen-form of the crystalline borosilicate was exchanged with the appropriate metal salt at a temperature of 194° F. (90° C.) for a period of about 90 to about 120 minutes, filtered, washed, dried, and program calcined at a temperature of 1,000° F. (538° C.). The metal-exchanged borosilicate was mixed with PHF-alumina hydrosol (9 wt.% solids) obtained from the American Cyanamid Company in a Waring Blendor and gelled with aqueous ammonia. The resulting gel was dried and calcined at a temperature of 1,000° F. (538° C.) for a period of 12 hours. In each case, the resulting catalyst, which contained 50 wt.% crystalline borosilicate and 50 wt.% gamma-alumina, was then ground to a 18-to-40-mesh material, i.e., a material that would pass through an 18-mesh screen (U.S. Sieve Series) but would be retained upon a 40-mesh screen (U.S. Sieve Series).

In the case of the impregnated samples, the hydrogen form of the borosilicate was incorporated into a catalyst as described in the paragraph hereinabove. The 18-to-40-mesh particles were then impregnated using 1 ml of an aqueous solution of the appropriate metal salt per gram of catalyst. The resulting samples were than dried and calcined at 1,000° F. (538° C.) for a period of 12 hours. The drying was conducted in a forced draft oven for a period of 16 hours at a temperature of 329° F. (165° C.).

Table XIV lists various catalysts that were prepared according to the descriptions provided hereinabove and in Examples VII and VIII. The particular metal salt that was employed in the cation-exchanging or the impregnation and the technique of incorporation are listed for each catalyst.

TABLE XIV

| Example | IX | X | XI | XII | XIII | XIV | XV | XVI |
|---|---|---|---|---|---|---|---|---|
| Catalyst | E | F | G | H | I | J | K | L |
| Metal Source | — | — | — | Calcium Acetate | $H_3BO_3$ | $Zn(NO_3)_2$ | $Cr(OAc)_3$ | $Cr(OAc)_3$ |
| Metal Impregnated | — | — | — | — | B | — | Cr | Cr |
| Metal Exchanged | — | — | Na | Ca | — | Zn | — | — |
| Amount of Metal, % | | | 0.59 | 0.23 | 1.5 | 0.15 | 0.34 | 1.7 |
| Test No. | 5 | 6 | 7 | 8 | 9 | 10 | 11 | 12 |
| Conditions: | | | | | | | | |
| Temp., °F. | 750 | 750 | 750 | 750 | 750 | 750 | 750 | 750 |
| °C. | 399 | 399 | 399 | 399 | 399 | 399 | 399 | 399 |
| Press., psig | 200 | 200 | 200 | 200 | 200 | 200 | 200 | 200 |
| KPa | 1,480 | 1,480 | 1,480 | 1,480 | 1,480 | 1,480 | 1,480 | 1,480 |
| Contact Time, sec | 5.2 | 5.0 | 5.7 | 4.5 | 4.9 | 4.4 | 4.9 | 4.9 |
| Time on Oil, hrs | 30 | 6 | 5 | 6 | 106 | 5 | 24 | 45.5 |
| Hydrogen/HC | 5.6 | 6.6 | 7.5 | 7.1 | 6.0 | 7.1 | 6.6 | 4.5 |
| Data/Pass | | | | | | | | |
| p-Xylene PATE | 99+ | 99+ | 99+ | 99+ | 99+ | 99+ | 99+ | 99+ |
| % Ethylbenzene Loss | 23.3 | 25.3 | 12.2 | 16.8 | 15.8 | 19.9 | 20.7 | 21.3 |
| % Xylene Loss | 2.8 | 3.6 | 0.8 | 2.4 | 1.9 | 1.5 | 1.0 | 0.5 |
| Ethylbenzene/Xylene Loss | 8.4 | 7.0 | 15.0 | 7.0 | 8.3 | 13.0 | 20.7 | 42.6 |
| Products | | | | | | | | |
| Paraffins and Naphthenes | 0.01 | 0.02 | 0.00 | 0.00 | 0.00 | 0.14 | 0.18 | 0.02 |
| Benzene | 2.22 | 2.89 | 1.17 | 2.05 | 1.96 | 2.29 | 2.83 | 2.45 |
| Toluene | 0.38 | 0.47 | 0.26 | 0.51 | 0.45 | 0.59 | 0.53 | 0.32 |
| $C_9+$ | 3.29 | 3.46 | 1.65 | 2.6 | 2.3 | 2.3 | 1.22 | 1.89 |

| Example | XVII | XVIII | XIX | XX | XXI | XXII | XXIII |
|---|---|---|---|---|---|---|---|
| Catalyst | L* | M* | N* | N | O | P | Q |
| Metal Source | $Cr(OAc)_3$ | $(NH_4)_6-Mo_7O_{24}$ | $(NH_4)_6-Mo_7O_{24}$ | $(NH_4)_6-Mo_7O_{24}$ | $Fe(NO_3)_3$ | $RuCl_3$ | $Co(NO_3)_2$ |
| Metal Impregnated | Cr | Mo | Mo | Mo | Fe | Ru | — |
| Metal Exchanged | — | — | — | — | — | — | Co |
| Amount of Metal, % | 1.7 | 3.3 | 5 | 5 | 3.5 | 0.5 | 0.06 |
| Test No. | 13 | 14 | 15 | 16 | 17 | 18 | 19 |
| Conditions: | | | | | | | |
| Temp., °F. | 750 | 750 | 750 | 750 | 750 | 750 | 750 |
| °C. | 399 | 399 | 399 | 399 | 399 | 399 | 399 |
| Press., psig | 200 | 200 | 200 | 200 | 200 | 200 | 200 |
| KPa | 1,480 | 1,480 | 1,480 | 1,480 | 1,480 | 1,480 | 1,480 |
| Contact Time, sec | 4.8 | 5.0 | 5.3 | 5.2 | 4.1 | 4.3 | 5.1 |
| Time on Oil, hrs | 92 | 98 | 113 | 24 | 21 | 24 | 30 |
| Hydrogen/HC | 4.9 | 5.4 | 5.5 | 5.3 | 5.2 | 7.0 | 6.1 |
| Data/Pass | | | | | | | |
| p-Xylene PATE | 99+ | 99+ | 99+ | 99+ | 99+ | 99+ | 99+ |
| % Ethylbenzene Loss | 16.9 | 23.2 | 28.7 | 22.9 | 14.8 | 26.7 | 17.6 |
| % Xylene Loss | 0.7 | 0.4 | 0.4 | 0.9 | 1.0 | 0.4 | 1.4 |
| Ethylbenzene/Xylene Loss | 24.1 | 56 | 72 | 25 | 14.8 | 63 | 12.3 |
| Products | | | | | | | |
| Paraffins and Naphthenes | 0.04 | 0.09 | 0.08 | 0.27 | 0.01 | 0.06 | 0.01 |
| Benzene | 2.15 | 3.3 | 3.9 | 3.25 | 1.52 | 3.30 | 1.81 |
| Toluene | 0.28 | 0.39 | 0.55 | 0.59 | 0.24 | 0.35 | 0.33 |
| $C_9+$ | 1.43 | 1.07 | 1.31 | 1.09 | 2.10 | 1.37 | 2.79 |

| Example | XXV | XXVI | XXVII | XXVIII | XXIX | XXX | XXXI | XXXII |
|---|---|---|---|---|---|---|---|---|
| Catalyst | R* | S | T* | U* | V* | W* | X | Y |
| Metal Source | $Co(NO_3)_2$ | $Ni(NO_3)_2$ | $Ni(OAc)_2$ | $Ni(NO_3)_2/NH_4OH$ | $Ni(NO_3)_2$ | $Ni(NO_3)_2$ | $RhCl_3$ | $RhCl_3$ |
| Metal Impregnated | Co | — | — | — | Ni | Ni | — | — |
| Metal Exchanged | — | Ni | Ni | Ni | — | — | Rh | Rh |
| Amount of Metal, % | 1.5 | 0.05 | 1.13 | 0.71 | 1.2 | 1 | — | — |
| Test No. | 21 | 22 | 23 | 24 | 25 | 26 | 27 | 28 |
| Conditions: | | | | | | | | |
| Temp., °F. | 750 | 750 | 750 | 750 | 750 | 750 | 750 | 785 |
| °C. | 399 | 399 | 399 | 399 | 399 | 399 | 399 | 419 |
| Press., psig | 200 | 200 | 200 | 200 | 200 | 200 | 200 | 200 |
| Kpa | 1,480 | 1,480 | 1,480 | 1,480 | 1,480 | 1,480 | 1,480 | 1,480 |
| Contact Time, sec | 4.9 | 5.3 | 5.5 | 4.3 | 5.0 | 5.2 | 6.0 | 4.0 |
| Time on Oil, hrs | 96 | 30 | 101 | 92 | 101 | 99 | 6 | 29 |
| Hydrogen/HC | 5.4 | 5.7 | 6.5 | 7.2 | 6.6 | 5.7 | 6.1 | 8.1 |

TABLE XIV-continued

| Data/Pass | | | | | | | | |
|---|---|---|---|---|---|---|---|---|
| p-Xylene PATE | 99+ | 99+ | 99+ | 99+ | 99+ | 99+ | 99+ | 99+ |
| % Ethylbenzene Loss | 29.6 | 20.3 | 17.6 | 10.6 | 29.1 | 30.5 | 18.3 | 28.2 |
| % Xylene Loss | 2.5 | 1.6 | 1.5 | 1.1 | 1.6 | 1.45 | 0.9 | 0.9 |
| Ethylbenzene/Xylene Loss | 11.8 | 13.0 | 11.6 | 9.6 | 17.9 | 21.1 | 19.7 | 30.5 |
| Products | | | | | | | | |
| Paraffins and Naphthenes | 0.04 | 0.01 | 0.09 | 0.01 | 0.07 | 0.12 | 0.02 | 0.02 |
| Benzene | 3.40 | 2.00 | 2.30 | 1.26 | 3.60 | 4.01 | 2.52 | 3.45 |
| Toluene | 0.55 | 0.37 | 0.60 | 0.35 | 0.70 | 0.69 | 0.37 | 0.69 |
| $C_9+$ | 3.6 | 2.9 | 1.71 | 1.56 | 2.66 | 2.33 | 1.75 | 2.39 |

| Example | XXXIII | XXXIV | XXXV | XXXVI | XXXVII | XXXVIII | XXXIX | XL |
|---|---|---|---|---|---|---|---|---|
| Catalyst | Z* | AA* | BB | CC | DD | EE | FF | GG |
| Metal Source | RhCl$_3$ | RhCl$_3$ | PdCl$_2$ | Pd(NO$_3$)$_2$ | Pd(NO$_3$)$_2$ | Pt(NH$_3$)$_4$Cl$_2$ | H$_2$PtCl$_6$ | H$_2$PtCl$_6$/ |
| Metal Impregnated | Rh | Rh | — | Pd | Pd | — | Pt | Pt |
| Metal Exchanged | — | — | Pd | — | — | Pt | — | — |
| Amount of Metal, % | 0.5 | 0.5 | — | 0.5 | 0.5 | 2.09 | 0.5 | 0.5 |
| Test No. | 29 | 30 | 31 | 32 | 33 | 34 | 35 | 36 |
| Conditions: | | | | | | | | |
| Temp., °F. | 750 | 800 | 800 | 750 | 800 | 800 | 800 | 750 |
| °C. | 399 | 427 | 427 | 399 | 427 | 427 | 427 | 399 |
| Press., psig | 200 | 200 | 200 | 200 | 200 | 200 | 200 | 200 |
| KPa | 1,480 | 1,480 | 1,480 | 1,480 | 1,480 | 1,480 | 1,480 | 1,480 |
| Contact Time, sec | 5.1 | 3.3 | 3.2 | 4.8 | 2.8 | 3.7 | 3.4 | 5.1 |
| Time on Oil, hrs | 101 | 96 | 28 | 39 | 28 | 24 | 22 | 5.5 |
| Hydrogen/HC | 5.8 | 6.1 | 7.2 | 9.7 | 6.3 | 8.3 | 8.0 | 6.2 |
| Data/Pass | | | | | | | | |
| p-Xylene PATE | 99+ | 99+ | 99+ | 99+ | 99+ | 99+ | 99+ | 99+ |
| % Ethylbenzene Loss | 29.5 | 33.6 | 31.7 | 29.3 | 35.1 | 37.1 | 43.7 | 59.4 |
| % Xylene Loss | 3.1 | 0.6 | 0.7 | 2.0 | 0.04 | −0.23 | 0.9 | 6.3 |
| Ethylbenzene/Loss Loss | 9.4 | 55 | 45.3 | 14.6 | 885 | −157 | 50 | 9.4 |
| Products | | | | | | | | |
| Paraffins and Naphthenes | 3.81 | 1.06 | 0.14 | 2.5 | 0.50 | 1.90 | 5.52 | 12.1 |
| Benzene | 3.14 | 4.38 | 4.43 | 3.3 | 4.89 | 3.98 | 3.35 | 2.94 |
| Toluene | 0.39 | 0.60 | 0.60 | 0.4 | 0.56 | 0.60 | 0.59 | 0.46 |
| $C_9+$ | 0.87 | 0.84 | 1.32 | 1.0 | 0.77 | 1.21 | 1.60 | 0.79 |

| Example | XLI | XLII | XLIII | XLIV | XLV |
|---|---|---|---|---|---|
| Catalyst | HH | II* | JJ* | KK* | LL* |
| Metal Source | H$_2$PtCl$_6$/ NH$_4$OH WASH | Mo—W | — | — | — |
| Metal Impregnated | Pt | — | Mo—Co | Mo—Ni | Ni—Cr |
| Metal Exchanged | — | — | — | — | — |
| Amount of Metal, % | 0.5 | 3.5 Mo— 2.5 W | 3.5 Mo— 1.5 W | 3.5 Mo— 1 Ni | 1 Ni— 1.7 Cr |
| Test No. | 37 | 38 | 39 | 40 | 41 |
| Conditions: | | | | | |
| Temp., °F. | 800 | 750 | 750 | 750 | 750 |
| °C. | 427 | 399 | 399 | 399 | 399 |
| Press., psig | 200 | 200 | 200 | 200 | 200 |
| KPa | 1,480 | 1,480 | 1,480 | 1,480 | 1,480 |
| Contact Time, sec | 2.6 | 4.8 | 4.9 | 4.8 | 4.6 |
| Time on Oil, hrs | 20.5 | 96 | 121 | 118 | 92.5 |
| Hydrogen/HC | 10.0 | 4.7 | 6.0 | 5.1 | 5.6 |
| Data/Pass | | | | | |
| p-Xylene PATE | 99+ | 99+ | 99+ | 99+ | 99+ |
| % Ethylbenzene Loss | 46.5 | 24.9 | 24.9 | 24.3 | 15.9 |
| % Xylene Loss | 0.2 | 0.5 | 0.5 | 1.2 | 0.4 |
| Ethylbenzene/Xylene Loss | 220 | 49.8 | 49.8 | 20.3 | 39.7 |
| Products | | | | | |
| Paraffins and Naphthenes | 4.43 | 0.06 | 0.08 | 0.17 | 0.29 |
| Benzene | 3.80 | 3.38 | 3.34 | 3.39 | 2.17 |
| Toluene | 0.61 | 0.48 | 0.54 | 0.62 | 0.27 |
| $C_9+$ | 1.01 | 1.36 | 1.38 | 1.42 | 0.83 |

*Sulfided.

In each of the Examples IX through XLV, the percent approach to equilibrium (PATE) for p-xylene is approximately equal to 99+. However, generally, the selectivity of a particular catalyst, i.e., the ethylbenzene loss/xylene loss, is large for those catalysts which had a catalytically active metal impregnated thereon. The most preferred catalyst was the catalyst into which molybdenum was impregnated, i.e., Catalyst M and Catalyst N, particularly when the catalyst had been pre-sulfided. Other suitable catalysts were Catalyst P, a ruthenium-impregnated catalyst, and Catalyst II, Catalyst JJ, and Catalyst LL, each of which had been impregnated with two metals.

What is claimed is:

1. A process for the conversion of a hydrocarbon stream, which process comprises contacting said stream at conversion conditions with a catalytic composition comprising a crystalline borosilicate and a porous refractory inorganic oxide, said borosilicate and said inorganic oxide having been intimately admixed with one another, said borosilicate comprising a molecular sieve material providing an X-ray diffraction pattern comprising the following X-ray diffraction lines and assigned strengths:

| d(Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

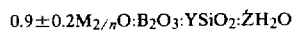

$$0.9 \pm 0.2 M_{2/n}O : B_2O_3 : Y SiO_2 : Z H_2O$$

wherein M is at least one cation having a valence of n, Y is between 4 and about 600, and Z is between 0 and about 160.

2. A process for the conversion of a hydrocarbon stream, which process comprises contacting said stream at conversion conditions with a catalytic composition comprising at least one catalytically-active metal and a catalytic support comprising a crystalline borosilicate suspended in and distributed throughout a matrix of a refractory inorganic oxide, which composition has been prepared by the method which comprises: (1) admixing said crystalline borosilicate in a finely-divided state with a hydrosol, sol, or hydrogel of said inorganic oxide in order to uniformly disperse said borosilicate in said hydrosol, sol, or hydrogel of said inorganic oxide to form an admixture, said borosilicate comprising a molecular sieve material providing an X-ray diffraction pattern comprising the following X-ray diffraction lines and assigned strengths:

| d(Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

$$0.9 \pm 0.2 M_{2/n}O : B_2O_3 : Y SiO_2 : Z H_2O$$

wherein M is at least one cation, n is the valence of the cation, Y is a value within the range of 4 to about 600, and Z is a value within the range of 0 to about 160; (2) while continually stirring the admixture, adding a gelling medium to promote gellation and to form a gel; (3) drying said gel at a temperature of about 77° F. (25° C.) to about 392° F. (200° C.) for a period of about 10 minutes to about 100 hours in the presence of air to form a dried mixture; (4) calcining said dried mixture by heating said dried mixture in air at a maximum rate of 200° F. per hour (111° C. per hour) to a calcination temperature within the range of about 752° F. (400° C.) to about 1,112° F. (600° C.) and maintaining said dried material at said calcination temperature for a period of about 30 minutes to about 20 hours to provide a calcined catalytic support material; (5) impregnating said calcined catalytic support material with a solution of a heat-decomposable compound of said catalytically-active metal to provide an impregnated material; (6) drying said impregnated material at a temperature of about 77° F. (25° C.) to about 392° F. (200° C.) for a period of about 10 minutes to about 100 hours in air to obtain a dried impregnated material; and (7) calcining said dried impregnated material by heating said dried impregnated material in air at a maximum rate of 200° F. per hour (111° C. per hour) to a calcination temperature within the range of about 752° F. (400° C.) to about 1,112° F. (600° C.) and maintaining said dried impregnated material at said calcination temperature for a period of about 30 minutes to about 20 hours to provide said catalytic composition.

3. A process for the catalytic isomerization of a xylene feed, which process comprises contacting said feed at isomerization conditions with a catalytic composition comprising a crystalline borosilicate and a porous refractory inorganic oxide, said borosilicate and said inorganic oxide having been intimately admixed with one another, said borosilicate comprising a molecular sieve material providing an X-ray diffraction pattern comprising the following X-ray diffraction lines and assigned strengths:

| d(Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

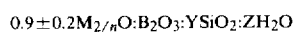

$$0.9 \pm 0.2 M_{2/n}O : B_2O_3 : Y SiO_2 : Z H_2O$$

wherein M is at least one cation having a valence of n, Y is between 4 and about 600, and Z is between 0 and about 160.

4. The process of claim 3, wherein said isomerization conditions comprise a temperature of about 200° F. (93° C.) to about 1,000° F. (538° C.), a hydrogen-to-hydrocarbon mole ratio of about 0 to about 20, a weight hourly space velocity (WHSV) of about 0.01 weight unit of feed per hour per weight unit of catalyst (hr$^{-1}$) to about 90 hr$^{-1}$, and a pressure of about 0 psig (101 KPa) to about 1,000 psig (6,998 KPa).

5. A process for the catalytic isomerization of a xylene feed, which process comprises contacting said feed at isomerization conditions with a catalytic composition comprising at least one catalytically-active metal and a catalytic support comprising a crystalline borosilicate suspended in and distributed throughout a matrix of a refractory inorganic oxide, which composition has been prepared by the method which comprises: (1) admixing said crystalline borosilicate in a finely-divided state with a hydrosol, sol, or hydrogel of said inorganic oxide in order to uniformly disperse said borosilicate in said hydrosol, sol, or hydrogel of said inorganic oxide to form an admixture, said borosilicate comprising a molecular sieve material providing an X-ray diffraction pattern comprising the following X-ray diffraction lines and assigned strengths:

| d(Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | and having the following composition in terms of mole ratios of oxides:

$$0.9 \pm 0.2 M_{2/n}O : B_2O_3 : YSiO_2 : ZH_2O$$

wherein M is at least one cation, n is the valence of the cation, Y is a value within the range of 4 to about 600, and Z is a value within the range of 0 to about 160; (2) while continually stirring the admixture, adding a gelling medium to promote gellation and to form a gel; (3) drying said gel at a temperature of about 77° F. (25° C.) to about 392° F. (200° C.) for a period of about 10 minutes to about 100 hours in the presence of air to form a dried mixture; (4) calcining said dried mixture by heating said dried mixture in air at a maximum rate of 200° F. per hour (111° C. per hour) to a calcination temperature within the range of about 752° F. (400° C.) to about 1,112° F. (600° C.) and maintaining said dried material at said calcination temperature for a period of about 30 minutes to about 20 hours to provide a calcined catalytic support material; (5) impregnating said calcined catalytic support material with a solution of a heat-decomposable compound of said catalytically-active metal to provide an impregnated material; (6) drying said impregnated material at a temperature of about 77° F. (25° C.) to about 392° F. (200° C.) for a period of about 10 minutes to about 100 hours in air to obtain a dried impregnated material; and (7) calcining said dried impregnated material by heating said dried impregnated material in air at a maximum rate of 200° F. per hour (111° C. per hour) to a calcination temperature within the range of about 752° F. (400° C.) to about 1,112° F. (600° C.) and maintaining said dried impregnated material at said calcination temperature for a period of about 30 minutes to about 20 hours to provide said catalytic composition.

6. The process of claim 5, wherein said isomerization conditions comprise a temperature of about 200° F. (93° C.) to about 1,000° F. (538° C.), a hydrogen-to-hydrocarbon mole ratio of about 0 to about 20, a weight hourly space velocity (WHSV) of about 0.01 weight unit of feed per hour per weight unit of catalyst (hr$^{-1}$) to about 90 hr$^{-1}$, and a pressure of about 0 psig (101 KPa) to about 1,000 psig (6,998 KPa).

7. The process of claim 1, wherein at least one catalytically-active metal has been cation-exchanged onto said borosilicate.

8. The process of claim 7, wherein said at least one catalytically-active metal is nickel.

9. The process of claim 2, wherein at least one catalytically-active metal has been cation-exchanged onto said borosilicate.

10. The process of claim 2, wherein the impregnated catalytically-active metal is molybdenum, tungsten, cobalt, or nickel.

11. The process of claim 9, wherein the impregnated catalytically-active metal is molybdenum, tungsten, cobalt, or nickel.

12. The process of claim 4, wherein at least one catalytically-active metal has been cation-exchanged onto said borosilicate.

13. The process of claim 12, wherein said at least one catalytically-active metal is nickel.

14. The process of claim 5, wherein at least one catalytically-active metal has been cation-exchanged onto said borosilicate.

15. The process of claim 5, wherein the impregnated catalytically-active metal is molybdenum, tungsten, cobalt, or nickel.

16. The process of claim 6, wherein at least one catalytically-active metal has been cation-exchanged onto said borosilicate.

17. The process of claim 6, wherein the impregnated catalytically-active metal is molybdenum, tungsten, cobalt, or nickel.

18. The process of claim 14, wherein the impregnated catalytically-active metal is molybdenum, tungsten, cobalt, or nickel.

19. The process of claim 15, wherein the impregnated catalytically-active metal is molybdenum.

20. The process of claim 16, wherein the impregnated catalytically-active metal is molybdenum, tungsten, cobalt, or nickel.

21. The process of claim 17, wherein the impregnated catalytically-active metal is molybdenum.

22. The process of claim 18, wherein the cation-exchanged metal is nickel.

23. The process of claim 20, wherein the cation-exchanged metal is nickel.

* * * * *